(12) United States Patent
Zur Hausen et al.

(10) Patent No.: US 11,718,662 B2
(45) Date of Patent: Aug. 8, 2023

(54) REP PROTEIN AS PROTEIN ANTIGEN FOR USE IN DIAGNOSTIC ASSAYS

(71) Applicant: DEUTSCHES KREBSFORSCHUNGSZENTRUM STIFTUNG DES OFFENTLICHEN RECHTS, Heidelberg (DE)

(72) Inventors: Harald Zur Hausen, Waldmichelbach (DE); Ethel-Michele De Villiers-Zur Hausen, Waldmichelbach (DE); Timo Bund, Dossenheim (DE); Sebastian Eilebrecht, Eslohe (DE)

(73) Assignee: DEUTSCHES KREBSFORSCHUNGSZENTRUM STIFTUNG DES ÖFFENTLICHEN RECHTS, Heidelberg (DE)

( * ) Notice: Subject to any disclaimer, the term of this patent is extended or adjusted under 35 U.S.C. 154(b) by 824 days.

(21) Appl. No.: 16/376,154

(22) Filed: Apr. 5, 2019

(65) Prior Publication Data

US 2019/0270795 A1 Sep. 5, 2019

Related U.S. Application Data

(63) Continuation-in-part of application No. PCT/EP2017/075774, filed on Oct. 10, 2017.

(30) Foreign Application Priority Data

Oct. 10, 2016 (EP) .................................... 16193119

(51) Int. Cl.
| | |
|---|---|
| G01N 33/543 | (2006.01) |
| C07K 16/18 | (2006.01) |
| G01N 33/563 | (2006.01) |
| G01N 33/577 | (2006.01) |
| G01N 33/68 | (2006.01) |
| G01N 33/53 | (2006.01) |
| G01N 33/564 | (2006.01) |
| G01N 33/50 | (2006.01) |

(52) U.S. Cl.
CPC .......... *C07K 16/18* (2013.01); *G01N 33/502* (2013.01); *G01N 33/53* (2013.01); *G01N 33/563* (2013.01); *G01N 33/564* (2013.01); *G01N 33/577* (2013.01); *G01N 33/6857* (2013.01); *G01N 2496/80* (2013.01); *G01N 2800/285* (2013.01)

(58) Field of Classification Search
None
See application file for complete search history.

(56) References Cited

U.S. PATENT DOCUMENTS

| | | | | |
|---|---|---|---|---|
| 5,756,302 | A | * | 5/1998 | Milburn ............... C07K 16/085 435/5 |
| 10,907,141 | B2 | * | 2/2021 | Bund ..................... C12N 9/506 |
| 2003/0068806 | A1 | * | 4/2003 | Ayal-Hershkovitz ........................ C12Y 302/01166 435/201 |
| 2006/0105419 | A1 | * | 5/2006 | Blankenberg ............ C12Q 1/28 435/25 |

FOREIGN PATENT DOCUMENTS

| | | |
|---|---|---|
| EP | 2868751 A1 | 5/2015 |
| EP | 2966176 A1 | 1/2016 |

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Harlow, E. and Lane, D., Antibodies: A Laboratory Manual (1988) Cold Spring Harbor Laboratory Press, Cold Spring Harbor, NY, pp. 23-26. (Year: 1988).*
Lederman et al. "A single amino acid substitution in a common African allele of the CD4 molecule ablates binding of the monoclonal antibody, OKT4" Mol Immunol. Nov. 1991;28(11):1171-81. (Year: 1991).*
Colman et al. Research in Immunology, 1994; 145(1): 33-36. (Year: 1994).*
Ben-Fredj et al., Prevalence of human herpesvirus U94/REP antibodies and DNA in Tunisian multiple sclerosis patients, J neurovirol , 2013, 19, pp. 42-47. (Year: 2013).*
K. Gunst, et al., Isolation of Bacterial Plasmid-Related Replication-Associated Circular DNA from a Serum Sample of a Multiple Sclerosis Patient, Genome Announcements (Aug. 28, 2014) vol. 2, No. 4, e00847-14.
I. Lamberto, et al., Mycovirus-Like DNA Virus Sequences from Cattle Serum and Human Brain and Serum Samples from Multiple Sclerosis Patients, Genome Announcements, (Aug. 28, 2014) vol. 2, No. 4, e00848-14.
International Search Report dated Jan. 26, 2018 in International Application No. PCT/EP2017/075774.
Notification of Transmittal of The International Preliminary Report on Patentability dated Jan. 30, 2019 in International Application No. PCT/EP2017/075774.

* cited by examiner

*Primary Examiner* — Gary Counts
(74) *Attorney, Agent, or Firm* — Duane Morris LLP; Thomas J. Kowalski; Deborah L. Lu

(57) ABSTRACT

Disclosed is a method of diagnosing multiple sclerosis (MS), wherein a blood sample from a patient is incubated with a DNA-replication associated (REP) protein. The present invention relates to a DNA-replication-associated (Rep) protein for use in the diagnosis of multiple sclerosis (MS), wherein (a) an increased amount of Rep protein or fragments thereof in the sample as compared to an amount in a control sample; or an increased amount of anti-Rep protein antibodies with antigen in a sample from a subject as compared to an amount in a control sample correlates with a diagnosis of MS, wherein the Rep protein is MSBI1 Rep or MSBI2 Rep.

12 Claims, 7 Drawing Sheets

Specification includes a Sequence Listing.

```
optimized  ATGAGCGACCTGATCGTGAAAGACAATGCCCTGATGAACGCCTCCTACAACCTGGCACTG
original   ATGAGCGATTTAATAGTAAAAGATAACGCCCTAATGAATGCTAGTTATAACTTAGCTTTG
           ********  *   ***  *** *     * * optimized  GTCGAACAGAGACTGATTCTGCTGGCTATCATCGAGGCAAGGGAGACCGGCAAGGGCATC
original   GTTGAACAGAGGTTAATTCTATTAGCAATCATAGAAGCGACAGAAACAGGCAAAGGCATT
            ******  * *****  *  *         *  ** optimized  AACGCCAATGACCCCCTGACAGTGCACGCCAGCTCCTACATCAACCAGTTTAATGTGGAG
original   AATGCCAATGATCCTTTAACAGTTCATGCAAGTAGCTATATCAATCAATTTAACGTAGAA
            ****   * ***  **  *   *  * *   ** optimized  CGCCACACCGCCTATCAGGCCCTGAAGGACGCCTGCAAGGATCTGTTTGCCCGGCAGTTC
original   AGGCATACGGCATATCAAGCCCTCAAAGATGCTTGTAAAGACTTGTTTGCCCGTCAATTC
                * **        ******  *** optimized  AGCTACCAGGAGAAGCGGGAGAGAGGCAGGATCAACATCACAAGCAGATGGGTGTCCCAG
original   AGTTACCAAGAAAAGCGAGAACGAGGACGAATTAATATTACAAGTCGATGGGTTTCGCAA
             *  **  * ****    *    ** ***   * optimized  ATCGGCTATATGGACGATACCGCCACAGTGGAGATCATCTTTGCCACCAGCAGTGGTGCCT
original   ATTGGCTATATGGACGATACAGCAACCGTTGAGATTATTTTTGCCCCTGCGGTTGTTCCT
            ***************    ***  ****  *** * *** optimized  CTGATCACCAGGCTGGAGGAGCAGTTCACACAGTACGACATCGAGCAGATCTCCGGACTG
original   CTGATTACACGGCTAGAGGAACAGTTCACCCAGTACGATATTGAGCAAATTAGCGGTTTA
           ***  * **   * *****  **  * **    * * *  * optimized  TCTAGCGCCTACGCCGTGCGCATGTATGAGCTGCTGATCTGTTGGCGGTCTACCGGCAAG
original   TCGAGTGCATATGCTGTTCGTATGTACGAACTGCTGATTTGTTGGCGTAGCACAGGCAAA
           **  *      * **    ***** ****      ***** optimized  ACACCTATCATCGAGCTGGATGAGTTCCGCAAGCGGATCGGCGTGCTGGACACCGAGTAC
original   ACACCAATTATTGAGCTAGACGAGTTTAGAAAGCGAATAGGTGTTTTAGATACTGAATAC
           ***   *   **    *        * * *** optimized  ACCAGAACAGATAACCTGAAGATGAGAGTGATCGAGCTGGCCCTGAAGCAGATCAATGAG
original   ACTAGAACAGATAATTTAAAGATGCGAGTTATTGAATTAGCCCTAAAACAAATCAACGAA
            ********  *  * *** * *    **  ** * optimized  CACACCGATATCACAGCCTCTTATGAGCAGCACAAGAAGGGCCGCGTGATCACCGGCTTC
original   CATACAGACATCACAGCAAGCTATGAACAACACAAAAAAGGGCGAGTGATTACAGGATTC
              ****** * ****  ***  * *   * * optimized  AGCTTTAAGTTCAAGCACAAGAAGCAGAACTCTGACAAGACACCAAAGAATAGCGATTCC
original   TCATTCAAGTTTAAGCACAAGAAACAAAACAGCGATAAAACGCCAAAAAATAGCGATTCT
               * *******   *     **** ********* optimized  TCTCCCGGATCGTGAAGCACAGCCAGATCCCTACCAACATCGTGAAGCAGCCAGAGAAT
original   AGCCCACGTATCGTAAAACATAGTCAAATCCCTACCAACATTGTAAAACAGCCTGAAAC
             * ** *  ***      ***********   *  ** optimized  GCCAAGATGTCCGACCTGGAGCACAGGGCATCTAGGGTGACAGGCGAGATCATGAGAAAT
original   GCCAAATGAGCGATTTAGAACATAGAGCGAGCCGTGTTACAGGGGAAATAATGCGAAAT
           *** *  ***  *        ** * ****  * * **** optimized  AGCCTCAGCGATCGGTTCAAGCACGGCCACCGACTCCGCCATCGATATCATCAAGACAATC
original   CGTCTGTCAGATCGGTTTAAACAAGGCGATGAATCAGCAATCGACATGATGAAACGTATT
             * *         * * ** * ** * *     * * *   * optimized  CAGTCCGAGATCATCACCGACGCCATCGCCGATCAGTGGAATCTAAACTGGAAGAGTTT
original   CAAAGTGAAATAATAACCGATGCAATAGCAGACCAGTGGGAAAGCAAACTGGAGGAGTTT
           **    *    **     *  *******  * * ***** **** optimized  GGAGTCGTGTTTGGAGCACATCACCATCATCATCACTGA
original   GGCGTGGTTTTTTAG-----------------------
           ** ** ** ***  *** 
```

Figure 8

REP PROTEIN AS PROTEIN ANTIGEN FOR USE IN DIAGNOSTIC ASSAYS

RELATED APPLICATIONS AND INCORPORATION BY REFERENCE

This application is a continuation-in-part application of international patent application Serial No. PCT/EP2017/075774 filed 10 Oct. 2017, which published as PCT Publication No. WO 2018/069296 on 19 Apr. 2018, which claims benefit of European patent application Serial No. 16193119.1 filed 10 Oct. 2016.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, is named Y8005_00017SL.txt and is 22 Kbytes in size.

FIELD OF THE INVENTION

The invention relates to the detection and quantification of a DNA-replication-associated (Rep) protein or anti-Rep antibodies for use in the diagnosis of a neurodegenerative disease such as, for example, multiple sclerosis (MS). In particular, the invention relates to a MSBI1 genome-encoded Rep protein.

BACKGROUND OF THE INVENTION

The etiology of multiple sclerosis (MS) has not been resolved. Thus, there is a demand for a biomarker for MS which could be used for diagnosing MS and/or monitoring MS or a treatment of MS and/or assessing a predisposition for MS.

Multiple sclerosis (MS) is characterized by demyelinization of MS lesions damaging nerve cells in the brain and spinal cord. MS symptoms either occur as episodes of sudden worsening (relapses, exacerbations, bouts, attacks) or as a gradual worsening over time (progressive forms). Demyelinization starts inflammatory processes which trigger T cells and the release of cytokines and antibodies. For the diagnosis of MS, among others, neuroimaging, analysis of the cerebrospinal fluid and evoked potentials are used.

A spectrum of 17 different, but partially related DNA molecules were isolated from different test material (multiple sclerosis (MS) brain tissue, bovine sera, milk) (Funk, Gunst et al. 2014, Gunst, Zur Hausen et al. 2014, Lamberto, Gunst et al. 2014, Whitley, Gunst et al. 2014).

Among these isolates two DNA molecules closely related to transmissible spongiform encephalopathy (TSE)-associated isolate Sphinx 1.76 (1,758 bp; accession no. HQ444404, (Manuelidis L. 2011)) were isolated from brain tissue from MS patients. These isolates were MSBI1.176 (MSBI, multiple sclerosis brain isolate) (1,766 bp) and MSBI2.176 (1,766 bp) which are designated as "MSBI1 genome" and "MSBI2 genome", respectively. MSBI1,176 shares 98% nucleotide similarity to the sequence of Sphinx 1.76. The large open reading frames (ORFs) of the isolates encode a putative DNA replication protein sharing high similarity between them. Another common feature is the presence of iteron-like tandem repeats. The alignment of this repeat region indicates a variation in the core of single nucleotides. This iteron-like repeats may constitute the binding sites for Rep proteins. The sequences of the isolates have been deposited in the EMBL Databank under accession numbers LK931491 (MSBI1.176) and LK931492 (MSBI2.176) (Whitley C. et al. 2014) and have been aligned and described in WO 2016/005064.

Further isolates were obtained from cow milk. These Cow milk isolates (CMI) were CMI1.252, CMI2.214 and CMI3.168 which are designated as "CMI1 genome", "CMI2 genome" and "CMI3 genome", respectively. The sequences of the isolates have been deposited in the EMBL Databank under accession numbers LK931487 (CMI1.252), LK931488 (CMI2.214) and LK931489 (CMI3.168) and have been aligned and described in WO 2016/005064.

Citation or identification of any document in this application is not an admission that such document is available as prior art to the present invention.

SUMMARY OF THE INVENTION

The present inventors have found that MSBI1 genome shows a significant production of transcribed RNA and MSBI1 genome-encoded Rep protein is expressed in human cells. The present inventors have found that the MSBI1 and MSBI2 genome-encoded Rep protein (MSBI1 Rep and MSBI2 Rep) represent a biomarker for pathogenicity screening assays. As DNA-replication-associated protein (RepB) the Rep protein has DNA binding activity and can be essential for initiation of replication of episomal or viral DNA molecules. Rep proteins, which are structurally similar to the MSBI1 genome-encoded Rep according to the present invention, show a marked potential of self-oligomerization and aggregation, which was described within prokaryotic systems in vivo and in vitro (Giraldo, Moreno-Diaz de la Espina et al. 2011, Torreira, Moreno-Del Alamo et al. 2015).

The present invention provides a platform for pathogen-specific, diagnostic screening assays based on the use of a Rep protein as an antigen.

In certain embodiments anti-Rep antibodies are used as pathogenic markers due to the link of pathogenic activity of the isolated DNA (e.g. MSBI1) agent with the Rep protein expression. Patient sera containing increased amounts of anti-Rep antibodies indicate that the corresponding patient was definitely exposed to Rep-related proteins or himself expressed Rep during a time period long enough to initiate a Rep specific immune response. As target for the human antibodies Rep protein is used as the antigen. Based on the quantification of the amount of anti Rep antibodies acute MS as well as a predisposition for MS can be diagnosed or monitored. Because it has been recognized that increased amount of induced anti-Rep antibodies or expressed Rep protein in a sample indicates the onset and/or status of MS, the increased amount of anti-Rep antibodies and Rep protein, respectively, can be used as pathogenic biomarker for the diagnosis of MS.

Advantageously, the pathogenic biomarker for MS can be detected in blood samples, such as serum or plasma samples, and it is not necessary to obtain samples from the cerebrospinal fluid.

Hence, the invention provides a DNA-replication-associated (Rep) protein for use in the diagnosis of a neurodegenerative disease, for example, multiple sclerosis (MS). In certain embodiments, the Rep protein is encoded by the MSBI1 genome and may comprise (i) an amino acid sequence as depicted in SEQ ID NO:1; (ii) a fragment of SEQ ID NO:1 which is capable of binding an anti-Rep antibody specific for a protein which may comprise an amino acid sequences as depicted in SEQ ID NO: 1; or (iii) an amino acid sequence having a 90% or more homology to the amino acid sequence of (i) or (ii) and is capable of binding an anti-Rep antibody specific for a protein which may comprise an amino acid sequences as depicted in SEQ ID NO: 1.

In other embodiments the Rep protein is encoded by the MSBI2 genome and may comprise (i) an amino acid sequence as depicted in SEQ ID NO:8; (ii) a fragment of SEQ ID NO:8 which is capable of binding an anti-Rep antibody specific for a protein which may comprise an amino acid sequences as depicted in SEQ ID NO: 8; or (iii) an amino acid sequence having a 90% or more homology to the amino acid sequence of (i) or (ii) and is capable of binding an anti-Rep antibody specific for a protein which may comprise an amino acid sequences as depicted in SEQ ID NO: 8.

In other embodiments the Rep protein is encoded by the CMI1 genome and may comprise (i) an amino acid sequence as depicted in SEQ ID NO:10; (ii) a fragment of SEQ ID NO:10 which is capable of binding an anti-Rep antibody specific for a protein which may comprise an amino acid sequences as depicted in SEQ ID NO: 10; or (iii) an amino acid sequence having a 90% or more homology to the amino acid sequence of (i) or (ii) and is capable of binding an anti-Rep antibody specific for a protein which may comprise an amino acid sequences as depicted in SEQ ID NO: 10.

In other embodiments the Rep protein is encoded by the CMI2 genome and may comprise (i) an amino acid sequence as depicted in SEQ ID NO:11; (ii) a fragment of SEQ ID NO:11 which is capable of binding an anti-Rep antibody specific for a protein which may comprise an amino acid sequences as depicted in SEQ ID NO: 11; or (iii) an amino acid sequence having a 90% or more homology to the amino acid sequence of (i) or (ii) and is capable of binding an anti-Rep antibody specific for a protein which may comprise an amino acid sequences as depicted in SEQ ID NO: 11.

In other embodiments the Rep protein is encoded by the CMI3 genome and may comprise (i) an amino acid sequence as depicted in SEQ ID NO:12; (ii) a fragment of SEQ ID NO:12 which is capable of binding an anti-Rep antibody specific for a protein which may comprise an amino acid sequences as depicted in SEQ ID NO: 12; or (iii) an amino acid sequence having a 90% or more homology to the amino acid sequence of (i) or (ii) and is capable of binding an anti-Rep antibody specific for a protein which may comprise an amino acid sequences as depicted in SEQ ID NO: 12.

In certain embodiments an increased amount of Rep protein in a sample from a subject as compared to a Rep protein amount in a control sample correlates with a diagnosis of a neurodegenerative disease, e.g. MS, i.e. indicates MS. According to the present invention diagnosis of a neurodegenerative disease, e.g. MS or a predisposition for the neurodegenerative disease, e.g. MS, is indicated by an increased amount of Rep protein of at least 2 fold as compared to a control sample.

In other embodiments an increased amount of anti-Rep antibodies in a sample from a subject as compared to anti-Rep antibody amount in a control sample correlates with a diagnosis of a neurodegenerative disease, e.g. MS, i.e. is indicative for MS. According to the present invention diagnosis of a neurodegenerative disease, e.g. MS or a predisposition for a neurodegenerative disease, e.g. MS is indicated by an increased amount of anti-Rep antibodies of at least 2 fold as compared to a control sample.

The Rep protein of the present invention may be employed in virtually any assay format that employs a known antigen to detect antibodies or cell-mediated immune responses. Thus, the present invention also encompasses the detection of cell-mediated, e.g. T-cell immune responses against Rep protein.

In certain embodiments the invention provides a method of diagnosing a neurodegenerative disease in a subject which may comprise the steps of incubating a sample from a subject with a Rep protein; detecting the amount of antibodies in the sample from the subject forming an immunological complex with Rep protein; and correlating the amount of antibody bound to Rep protein, as compared to an amount in a control sample, with a diagnosis of a neurodegenerative disease.

In particular embodiments the invention provides a method of diagnosing MS in a subject which may comprise the steps of incubating a sample from a subject with a Rep protein; detecting the amount of antibodies in the sample from the subject forming an immunological complex with Rep protein; and correlating the amount of antibody bound to Rep protein, as compared to an amount in a control sample, with a diagnosis of MS.

In particular embodiments the Rep protein is immobilized, e.g. attached to a support or carrier, followed by incubating the immobilized Rep protein with the sample from the subject.

In other embodiments the Rep protein is expressed in cells followed by incubating the cells with the sample from the subject.

In certain embodiments the amount of antibodies forming an immunological complex with Rep protein is quantified by an additional binding agent coupled to a signal generating compound which is capable of binding to the anti-Rep antibodies of the immunological complex, for example a detectably labeled secondary antibody, preferably anti-human antibody.

In other embodiments the antibodies in the sample from the subject are immobilized followed by incubating with a defined amount of Rep protein.

Preferably, the sample from the subject and the control sample is a blood sample such as a serum or a plasma sample.

In other embodiments the invention provides a method of diagnosing a neurodegenerative disease in a patient which may comprise the steps of detecting the amount of Rep protein in a sample from a subject by anti-Rep antibodies, and correlating the amount of Rep protein detected in the sample from a subject in step (a) as compared to an amount in a control sample with a diagnosis of a neurodegenerative disease.

In certain embodiments the invention provides a method of diagnosing MS in a patient which may comprise the steps of detecting the amount of Rep protein in a sample from a subject by anti-Rep antibodies, and correlating the amount of Rep protein detected in the sample from a subject in step (a) as compared to an amount in a control sample with a diagnosis of MS.

In such embodiments the sample from a subject and the control sample are selected from the group consisting of a serum sample, plasma sample or tissue sample.

In particular embodiments the anti-Rep antibody binds to an epitope that is within an amino acid sequence selected from the group consisting of amino acids from 1 to 136, from 137 to 229 and from 230 to 324 of SEQ ID NO:1. For example, the antibody binds to an epitope which may comprise SEQ ID NO:2 or SEQ ID NO:3.

In further embodiments the invention provides a kit for use in the diagnosis of MS which may comprise (a) a Rep protein, in particular a MSBI1, a MSBI2, CMI1, CMI2 or CMI3 Rep protein, (b) an additional binding agent coupled to a signal generating compound, for example, an anti-human antibody coupled to a detectable label and capable of binding to anti-Rep antibody according to the invention, and (c) a solid matrix suitable for immobilizing a Rep protein according to (a) or anti-Rep antibodies, wherein aid antibodies are suspected in a sample, in particular a serum or a plasma sample.

In particular embodiments the kit is put together for use in an immunoassay, for example selected from the group consisting of enzyme-linked immunosorbent assay (ELISA), radioimmunoassay (RIA), enzyme immune assay (EIA), fluorescence immunoassay (FIA), luminescence immunoassay (LIA) and strip assay.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with Deutsche Sammlung für Mikroorganismen und Zellkulturen (DSMZ) [German Collection of Microorganisms and Cell Cultures], under deposit accession numbers DSM ACC3327, DSM ACC3328, DSM ACC3329, ACC3330 and antibody MSBI1 961-2-2 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 8 shows a sequence alignment of "optimized" (=SEQ ID NO:13) vs. "original" (=the wild-type; SEQ ID NO:15) MSBI1 sequence. The optimized codons are marked.

DETAILED DESCRIPTION OF THE INVENTION

Figure 1:
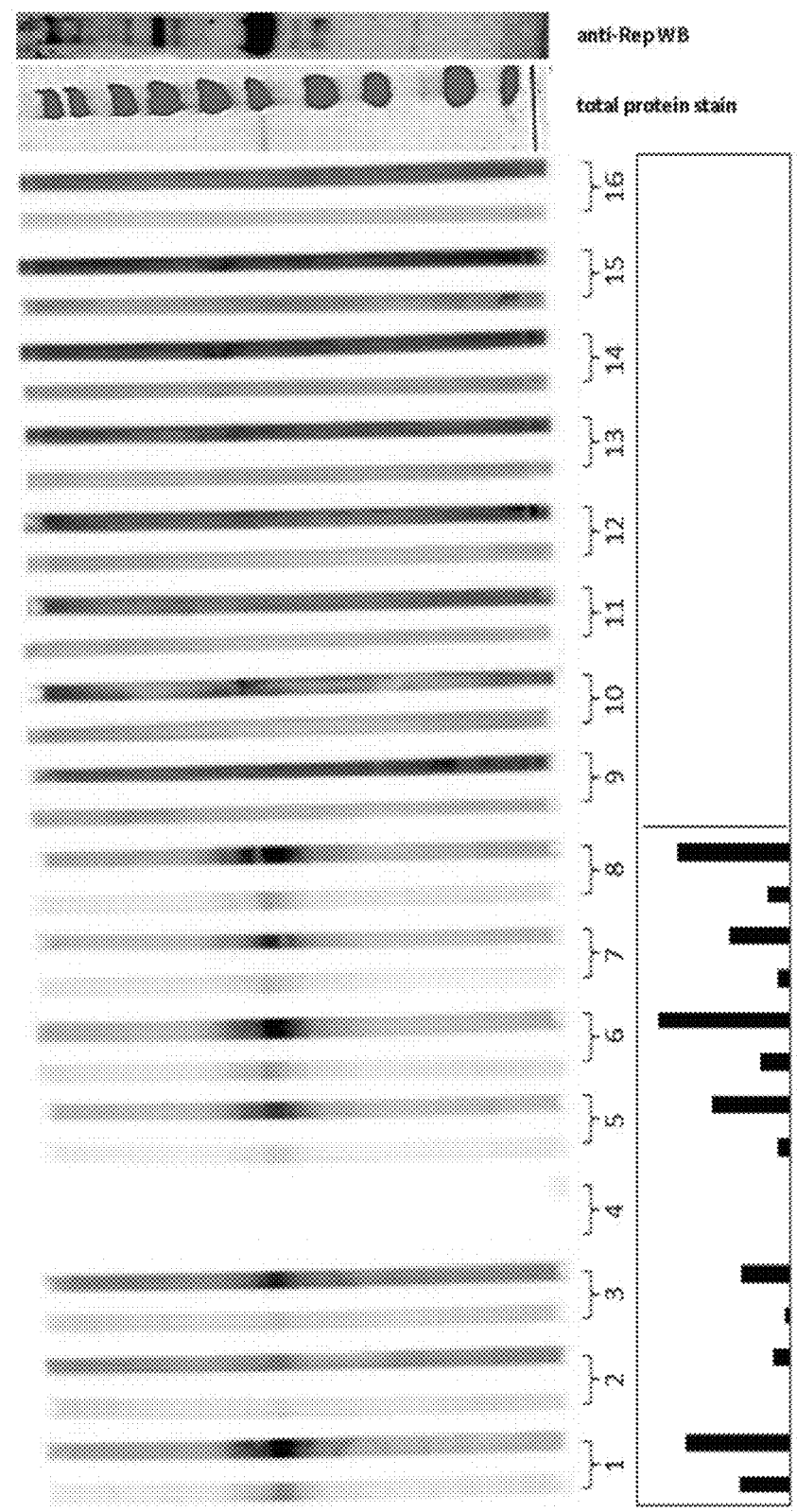
FIG. 1 shows an example serum screening of 2×8 samples by serum incubation of 1D-size-resolved Rep protein membrane stripes. Nitrocellulose stripes containing Rep protein were incubated with each two different serum/plasma dilutions (1:500 and 1:2000) of the MS serum sample pool or the healthy donor plasma pool. Rep-bound human IgGs were detected with anti-human IgG HRP-coupled secondary antibodies. Antibody signals at the size of the full-length Rep protein target (see Coomassie protein staining and anti-Rep WB controls on the right) were quantified by densitometry.

The invention provides diagnostic screening assays for the presence of anti-Rep antibodies as pathogenic markers. Samples containing increased amounts of anti-Rep antibodies indicate that the corresponding subject was definitely exposed to Rep-related protein or himself expressed Rep protein during a time period long enough to induce a Rep protein specific immune response. With such screening assays a diagnosis, prognosis and monitoring of MS based on the quantification of anti-Rep antibodies can be conducted. In alternative embodiments Rep protein may be directly detected and quantified in samples by anti-Rep antibodies.

"Rep protein" as used herein refers to a DNA-replication-associated protein (RepB). The Rep protein may comprise DNA binding activity and could be essential for initiation of replication of episomal/viral DNA molecules. In general Rep protein refers to a Rep protein from the group of the Small Sphinx Genome (Whitley et al., 2014). In particular, the Rep protein is a MSBI1 genome-encoded Rep protein (MSBI1 Rep), a MSBI2 genome-encoded Rep protein (MSBI2 Rep), a CMI1 genome-encoded Rep protein (CMI1 Rep), a CMI2 genome-encoded Rep protein (CMI2 Rep) or CMI3 genome-encoded Rep protein (CMI3 Rep). Preferably, the MSBI1 Rep protein is encoded by MSBI1.176 deposited in the EMBL databank under the acc. no. LK931491 and has the amino acid sequence as depicted in SEQ ID NO:1 or the Rep protein is MSBI2 encoded by MSBI2.176 deposited in the EMBL databank under the acc. no. LK931492 and has the amino acid sequence as depicted in SEQ ID NO:8 (Whitley, Gunst et al. 2014). In another preferred embodiment the CMI1 Rep protein is encoded by CMI1.252 deposited in the EMBL databank under the acc. no. LK931487 and has the amino acid sequence as depicted in SEQ ID NO:10. In another preferred embodiment the CMI2 Rep protein is encoded by CMI2.214 deposited in the EMBL databank under the acc. no. LK931488 and has the amino acid sequence as depicted in SEQ ID NO:11. In another preferred embodiment the CMI3 Rep protein is encoded by CMI3.168 deposited in the EMBL databank under the acc. no. LK931489 and has the amino acid sequence as depicted in SEQ ID NO:12. In a particular preferred embodiment the Rep protein may comprise a N-terminal region conserved among small Sphinx genomes consisting essentially of amino acids from 1 to 229 of SEQ ID NO:1 and a C-terminal variable region specific for MSBI1.176 consisting essentially from amino acids 230 to 324 of SEQ ID NO:1. The N-terminal conserved region may comprise a putative, first DNA binding domain consisting essentially of amino acids from 1 to 136 of SEQ ID NO: 1 and a second putative DNA binding domain consisting essentially of amino acids from 137 to 229 of SEQ ID NO:1.

"Rep protein" also encompasses fragments and variants of the protein with SEQ ID NO:1 or SEQ ID NO:8 which are capable of binding an anti-Rep antibody specific for Rep protein having the amino acid sequence of SEQ ID NO:1 or SEQ ID NO:8. Preferably, such a fragment is an immunogenic fragment of the protein having the amino acid sequence of SEQ ID NO:1 or SEQ ID NO:8 which encompasses at least one epitope for an anti-Rep protein antibody against the Rep protein of SEQ ID NO:1 or SEQ ID NO:8 and, preferably, may comprise at least 7, 8, 9, 10, 15, 20, 25 or 50 contiguous amino acids. In particular embodiments the fragment may comprise or consists essentially of a domain of the Rep protein, for example, the N-terminal conserved region, the C-terminal variable region, the first or second DNA binding domain. A variant of the protein with SEQ ID NO:1 or SEQ ID NO:8 may comprise one or more amino acid deletions, substitutions or additions compared to SEQ ID NO:1 and has a homology of at least 90%, 91%, 92%, 93%, 94%, 95%, 96%, 97%, 98% or 99% to the amino acid sequence of SEQ ID NO:1 or SEQ ID NO:8, wherein the variant is capable of binding an anti-Rep antibody specific for a Rep protein having the amino acid sequence of SEQ ID NO:1 or SEQ ID NO:8. Included within the definition of variant are, for example, polypeptides containing one or more analogues of an amino acid (including, for example, unnatural amino acids, peptide nucleic acid (PNA), etc.), polypeptides with substituted linkages, as well as other modifications known in the art, both naturally occurring and non-naturally occurring. The term Rep protein includes fusion proteins with a heterologous amino acid sequence, with a leader sequence or with a Tag-sequence and the like. In certain embodiments of the invention protein tags are genetically grafted onto the Rep protein described above, for example the Rep protein selected from the group consisting of MSBI1, MSBI2, CMI1, CMI2 or CMI3. In particular at least one protein tag is attached to a polypeptide consisting of an amino acid sequence as depicted in any one of SEQ ID NOs:1-3, 8-12, 14. Such protein tags may be removable by chemical agents or by enzymatic means. Examples of protein tags are affinity or chromatography tags for purification. For example the Rep protein may be fused to a Tag-sequence, for example, selected from the group consisting of His6-Tag (SEQ ID NO:4), T7-Tag (SEQ ID NO:5), FLAG-Tag (SEQ ID NO:6) and Strep-II-Tag (SEQ ID NO:7). a His-Tag (SEQ ID No:4), a T7-Tag (SEQ ID NO:5), FLAG-Tag (SEQ ID NO:6) or StrepII-Tag (SEQ ID NO:7). Further, fluorescence tags such as green fluorescence protein (GFP) or its variants may be attached to a Rep-protein according to the invention.

In a particular preferred embodiment the MSBI1 genome-encoded Rep protein (MSBI1 Rep) is codon-optimized for the production in human cell lines (e.g. HEK-293, HEK293TT, HEK293T, HEK293FT, HaCaT, HeLa, SiHa, CaSki, HDMEC, L1236, L428, BJAB, MCF7, Colo678, any primary cell lines) as well as bovine (e.g. MAC-T) or murine cell lines (e.g. GT1-7). As regards codon optimization, the nucleotide sequences that encode the antigens can be designed to employ codons that are used in the genes of the subject in which the antigen is to be produced. In a preferred embodiment, the codons used are "humanized" codons. Such codon usage provides for efficient expression of the antigens in human cells. Any suitable method of codon optimization may be used. Such methods and the selection of such methods are well known to those of skill in the art. According to the present invention, such a codon-optimized variant of the MSBI1 genome-encoded Rep protein (MSBI1 Rep) may comprise or has the sequence as depicted in SEQ ID. No.: 13 and may comprise or has the amino acid sequence as depicted in SEQ ID. No.: 14. In total, a number of 686 nucleotides of the 927 nucleotide MSBI1 Rep gene encoding for the Rep protein (from start to stop codon) were substituted to improve codon usage. A perfect codon usage with optimal adaptation towards e.g. the human codon usage is described by a codon adaptation index (CAI) of 1 indicating that all codons are optimized for human expression. For the original MSBI1-encoded Rep gene, a CAI of 0.67 for the human system was calculated, which is far below the a CAI of 0.8, which is considered as the lower threshold for good codon adaptation. After codon optimization of the MSBI1 rep gene, a CAI of 0.94 was calculated for the optimized DNA indicating an almost optimal codon adaptation for the human system. Especially, a number of 18 very rarely used codons were modified, most of them representing codons coding for leucine with a very low usage frequency (<10%) in the human system. A sequence alignment of the codon-optimized MSBI1 sequence of SEQ ID NO:13 vs. the wild-type MSBI1 sequence of SEQ ID NO:15 is shown in FIG. 8.

The Rep protein of the invention, including the Rep fragments and Rep variants as defined above, can be prepared by classical chemical synthesis. The synthesis can be carried out in homogeneous solution or in solid phase. The polypeptides according to this invention can also be prepared by means of recombinant DNA techniques. An example for producing and purification of a Rep protein according to the invention is shown in Example 1.

"Subject" as used herein refers to a mammalian individual or patient, including murines, cattle, for example bovines, simians and humans. Preferably, the subject is a human patient.

"Sample" as used herein refers to a biological sample encompassing liquid and solid samples. Liquid samples encompass blood liquids such as, for example, sera, plasma and cerebrospinal fluid (CSF). Solid samples encompass tissue samples such as tissue cultures or biopsy specimen.

"Correlates with" as used herein refers to an amount, i.e. level or titer, of anti-Rep antibodies and Rep protein, respectively, with a significant correlation with a disease status of, for example, MS. The correlation is determined by detecting the extent of difference in the amount present in a sample from a subject to be tested and a control sample. "Control sample" means a single sample or an average of various, i.e. more than two, control samples. The control is taken from a healthy individual who has not been diagnosed for MS. Alternatively, the correlation may be theoretically determined by detecting the extent of difference in the amount present in a sample for a subject to be tested with a predetermined cut-off value. A cut-off value is a reference value with statistically significant separation between different disease status, e.g. between healthy and diseased status. The cut-off value can be determined by statistical analysis of a sufficiently large panel of test samples from patients with disease history and samples from healthy test group by statistical tests known in the art.

In certain embodiments a diagnosis, for example of MS, is indicated by an at least 2 fold, 3 fold, 4 fold, 5 fold, 10 fold, 50 fold, 100 fold, 500 fold or 1000 fold increased amount of protein, i.e. Rep protein and anti-Rep-antibodies, respectively, in the sample from the subject as compared to a control sample.

"Anti-Rep antibody" as used herein refers to an antibody binding at a detectable level to Rep protein in the methods of the invention which affinity is more strongly to the Rep protein of the invention than to a non-Rep protein. Preferably, the antigen affinity for Rep protein is at least 2 fold larger than background binding. In particular the anti-Rep antibody is specific for the MSBI1 Rep having the amino acid sequence of SEQ ID NO:1 or MSBI2 Rep. In particular embodiments the antibody is cross-specific for MSBI1 Rep, MSBI2 Rep, CMI1 Rep, CMI2 Rep and/or CMI3 Rep. In certain embodiments the anti-Rep antibody is cross-specific for at least two, preferably all, off MSBI1 Rep, MSBI2 Rep, CMI1 Rep, CMI2 Rep and/or CMI3 Rep and binds to an epitope within amino acids from 1 to 136 of SEQ ID NO: 1.

A common feature of all assays is that the Rep protein is contacted with a sample suspected of containing anti-Rep protein antibodies under conditions that permit the Rep protein to bind to any such antibody present in the sample. Such conditions will typically be physiologic temperature, pH and ionic strength using an excess of Rep protein. The incubation of the Rep protein with the sample is followed by detection of immune complexes comprised of the antigen. In certain embodiments either the Rep protein is coupled to a signal generating compound, e.g. detectable label, or an additional binding agent, e.g. secondary anti-human antibody, coupled to a signal generating compound is used for detecting the immune complex.

Anti-Rep antibodies can be detected and quantified in assays based on Rep protein as protein antigen, which serves as target for the mammalian, e.g. human, antibodies suspected in the sample. Preferably, the Rep protein is purified (e.g. see Example 1) and the samples can be, for example, serum or plasma samples. The methods include immobilization of Rep protein on a matrix followed by incubation of the immobilized Rep protein with the samples. Finally, the Rep-bound antibodies of the formed immunological complex between Rep protein and antibodies of the samples are quantified by a detection binding agent coupled to a signal generating compound, e.g. secondary HRP-(horseradish-peroxidase)-coupled detection antibody allowing for HRP-substrate based quantification. This signal generating compound or label is in itself detectable or may be reacted with an additional compound to generate a detectable product.

In other embodiments anti-Rep antibodies are indirectly quantified in that first the antibodies of the sample are immobilized on a matrix, followed by incubation with a defined amount of Rep protein which may be labelled or comprise a Tag protein, wherein the anti-Rep antibodies immobilized and present on the matrix capture the Rep protein from the protein-sample liquid mixture, followed by quantification of the bound Rep protein.

In other embodiments Rep protein can be expressed in cells and these cells are incubated with the sample. Thereafter, anti-Rep antibodies from the sample bound to the Rep protein expressed by cells are detected and quantified.

Design of the immunoassay is subject to a great deal of variation, and many formats are known in the art. Protocols may, for example, use solid supports, or immunoprecipitation. Most assays involve the use of binding agents coupled to signal generating compounds, for example labelled antibody or labelled Rep protein; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be in a heterogeneous or in a homogeneous format, and of a standard or competitive type. In a heterogeneous format, the polypeptide (Rep protein or anti-Rep antibody) is typically bound to a solid matrix or support or carrier to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon), diazotized paper, nylon membranes, activated beads, and Protein A beads. The solid support containing the antigenic polypeptides is typically washed after separating it from the test sample, and prior to detection of bound anti-Rep antibodies. Both standard and competitive formats are known in the art.

In a homogeneous format, the test sample is incubated with the Rep protein in solution. For example, it may be under conditions that will precipitate any Rep protein-antibody complexes which are formed. Both standard and competitive formats for these assays are known in the art.

In a standard format, the amount of anti-Rep antibodies in the antibody-Rep protein complexes is directly monitored. This may be accomplished by determining whether (labelled) anti-xenogeneic (e.g. anti-human) antibodies which recognize an epitope on anti-Rep antibodies will bind due to complex formation. In a competitive format, the amount of anti-Rep antibodies in the sample is deduced by monitoring the competitive effect on the binding of a known amount of labelled antibody (or other competing ligand) in the complex.

Complexes formed which may comprise anti-Rep antibody (or in the case of competitive assays, the amount of competing antibody) are detected by any of a number of known techniques, depending on the format. For example, unlabeled anti-Rep antibodies in the complex may be detected using a conjugate of anti-xenogeneic Ig complexed with a label (e.g. an enzyme label, such as, for example, HRP).

In an immunoprecipitation or agglutination assay format the reaction between the Rep protein and the anti-Rep antibody forms a network that precipitates from the solution or suspension and forms a visible layer or film of precipitate. If no anti-Rep antibody is present in the sample, no visible precipitate is formed.

The solid phase selected can include polymeric or glass beads, nitrocellulose, microparticles, microwells of a reaction tray, test tubes and magnetic beads. The signal generating compound can include an enzyme, a luminescent compound, a chromogen, a radioactive element and a chemiluminescent compound. Examples of enzymes include alkaline phosphatase, horseradish peroxidase (HRP) and beta-galactosidase. Examples of enhancer compounds include biotin, anti-biotin and avidin. Examples of enhancer compounds binding members include biotin, anti-biotin and avidin.

In further embodiments the invention provides methods wherein an increased amount of Rep protein in a sample correlates with a diagnosis or predisposition of a neurodegenerative disease, for example MS, or is used for monitoring the disease, for example MS, or monitoring the treatment of the disease, for example MS. In such embodiments the Rep protein in the sample is detected by anti-Rep antibodies.

Such methods may comprise the steps of detecting the amount of Rep protein in a sample from a subject by anti-Rep antibodies; and correlating the amount of Rep protein detected in the sample from a subject in step (a) as compared to an amount in a control sample with a diagnosis of a neurodegenerative disease, for example MS.

Examples for assays which can be used in such methods for the detection of Rep protein in serum or plasma samples include, but are not limited to immunoprecipitation, immunofluoresence, dot blotting and Western Blot.

For example, a serum sample may be incubated with anti-Rep protein antibodies to capture the Rep protein in the sample, followed by a step of immunoprecipitation of Rep protein and, thereafter, a step of detection by SDS-PAGE and Western Blot.

In a further example, a dot blot membrane may be incubated with serum, followed by the step of a SDS-PAGE and Western Blot.

In a further example, serum dilutions of the sample are loaded on SDS-Page followed by a Western Blot.

In further embodiments Rep protein is detected in tissue samples by immunohistochemical methods or immunofluoresence microscopy.

In certain embodiments anti-Rep antibodies are used for the detection or capturing of the Rep protein in the sample.

The term "antibody", preferably, relates to antibodies which consist essentially of pooled polyclonal antibodies with different epitopic specificities, as well as distinct monoclonal antibody preparations. As used herein, the term "antibody" (Ab) or "monoclonal antibody" (Mab) is meant to include intact immunoglobulin molecules as well as antibody fragments (such as, for example, Fab and F(ab')2 fragments) which are capable of specifically binding to Rep protein. Fab and F(ab')2 fragments lack the Fc fragment of intact antibody, clear more rapidly from the circulation, and may have less non-specific tissue binding than an intact antibody. Thus, these fragments are preferred, as well as the products of a FAB or other immunoglobulin expression library. Moreover, antibodies useful for the purposes of the present invention include chimeric, single chain, multifunctional (e.g. bispecific) and humanized antibodies or human antibodies.

In certain embodiments the antibody or antigen binding fragment thereof is coupled to a signal generating compound, e.g., carries a detectable label. The antibody or antigen binding fragment thereof can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

Anti-Rep antibodies are, preferably, raised (generated) against a Rep protein having the amino acid sequence of SEQ ID NO:1 or SEQ ID NO:8 or a fragment thereof by methods well known to those skilled in the art.

In certain embodiments anti-Rep antibodies are used in the methods of the invention which are capable of binding to several or all kinds of Rep proteins from the group of the Small Sphinx Genome (anti-Small-Sphinx-like Rep antibody or anti-SSLRep antibody). Such anti-SSLRep antibody binds to an epitope within the conserved N-terminal region of the Rep protein from amino acids 1 to 229 of SEQ ID NO:1. In particular embodiments anti-Rep antibodies of the anti-SSLRep type are used which bind to an epitope within SEQ ID NO:2 (amino acids 32-49 of SEQ ID NO:1) or SEQ ID NO:3 (amino acids 197-216 of SEQ ID NO:1). The peptide fragments of SEQ ID NO:2 and SEQ ID NO:3 are highly conserved among the Rep proteins from the Small Sphinx Genome group and appear to be exposed due to their hydrophilic character. Anti-Rep antibodies of the anti-SSL-Rep type may be produced by immunization, for example of mice or guinea pig, by peptides consisting essentially of the amino acid sequences as depicted in SEQ ID NOs:2 or 3; or by other immunogenic fragments, preferably which may comprise at least 8-15 amino acids, derived from the conserved N-terminal Rep protein region from amino acids 1 to 229 of SEQ ID NO:1.

In further embodiments anti-Rep antibodies specific for MSBI1 Rep protein are used. Such antibodies may be produced, for example, by immunization of a mammal such as mice or guinea pig with a full-length Rep protein having the amino acid sequence of SEQ ID NO:1.

Preferably, the methods of the invention use anti-Rep antibodies which are capable of detecting Rep protein up to ranges from picogramm to femtogramm in different kinds of body liquids such as, for example, blood, serum, spinal fluid or cerebral fluid.

In the methods of the invention either a specific kind of anti-Rep antibody or a pool of two or more different kinds of anti-Rep antibodies may be used. If a pool of different kinds of anti-Rep antibodies is used, the anti-Rep antibody pool may comprise different anti-Rep antibodies binding to different epitopes within different domains of the Rep protein, e.g. first DNA binding domain (e.g. aa 1-136 of SEQ ID NO:1), second DNA binding domain (e.g. aa 137-229 of SEQ ID NO:2) and/or variable domain (e.g. aa 230-324 of SEQ ID NO:1), in particular, of MSBI1 Rep protein (SEQ ID NO:1).

In a further embodiment anti-Rep antibodies are used for screening of probes from patients and/or healthy individuals for a Rep protein. The selective detection of a Rep protein in tissues of patients, e.g. of a neurodegenerative disease, is indicative for a causality between the isolated DNA genome of the Rep protein detected in the sample and the disease of the patient from whom the sample was derived.

For the detection of a Rep protein by anti-Rep antibodies methods such as, for example, Western Blot, immunofluoresence microscopy or immunohistochemical methods may be applied.

In certain embodiments anti-Rep antibodies are used which are capable of detecting a Rep protein at certain celluar localisations. For instance the anti-Rep antibody may detect the Rep protein in cytoplasm, nuclear membrane and nucleus or detect speckles in cytoplasm. Examples of such groups of anti-Rep antibodies are shown in Table 1:

| Antibody Group | RepProtein Localisation | Specificity | Antibody | DSMZ deposit |
| --- | --- | --- | --- | --- |
| Group A | cytoplasm + nuclear membrane (+nucleus) | MSBI1 + small-sphinx-like | AB01 523-1-1 | DSM ACC3327 |
| Group B | speckles in cytoplasm | MSBI1 + small-sphinx-like | AB02 304-4-1 | DSM ACC3328 |
| Group C | cytoplasm + nuclear membrane (+nucleus) | MSBI1 specific | MSBI1 381-6-2 | DSM ACC3329 |
| Group D | speckles in cytoplasm | MSBI1 specific | D1: MSBI1 961-2-2 D2: MSBI1 761-5-1 | DSM ACC3330 |

Anti-Rep antibodies of group A have an epitope within the amino acid sequence depicted in SEQ ID NO:3 (aa 198-217 of SEQ ID NO:1) and are capable of detecting MSBI1 Rep and Rep proteins which may comprise this conserved epitope of the Small Sphinx Genome group (e.g. MSBI2, CMI1, CMI4). In immunofluoresence assays such anti-Rep antibodies detect a specific Rep localisation pattern, wherein the main localisation is homogeneously distributed over the cytoplasm and nuclear membrane; and additional weak and homogeneously distributed localisation is seen in the nucleus. An example of such a group A antibody is antibody AB01 523-1-1 (DSM ACC3327) which was employed in the examples as group A antibody.

Anti-Rep antibodies of group B have an epitope within the amino acid sequence depicted in SEQ ID NO:2 (aa 33-50 of SEQ ID NO:1) and are capable of detecting MSBI1 Rep and Rep proteins which may comprise this conserved epitope of the Small Sphinx Genome group (e.g. MSBI2, CMI1, CMI4). In immunofluoresence assays such anti-Rep antibodies detect specifically speckles (cytoplasmatic aggregations) of the Rep protein (often in the periphery of the nuclear membrane). An example of such a group B antibody is the antibody designated as AB02 304-4-1 (DSM ACC3328) which was employed in the examples as group B antibody.

Anti-Rep antibodies of group C detect specifically a structural epitope of MSBI1 (SEQ ID NO:1). In immunofluoresence assays such anti-Rep antibodies detect a specific Rep localisation pattern, wherein the main localisation is homogeneously distributed over the cytoplasm and nuclear membrane; and additional weak and homogeneously distributed localisation is seen in the nucleus. An example of such a group C antibody is antibody MSBI1 381-6-2 (DSM ACC3329) which was employed in the examples as group C antibody.

Anti-Rep antibodies of group D detect specifically a structural epitope of MSBI1 (SEQ ID NO:1), where antibody MSBI1 961-2-2 designated as "D1" detects an epitope depicted in SEQ ID NO:9 (aa 281-287) in the C-terminal domain of MSBI1. Antibody MSBI1 761-5-1 (DSM ACC3328) designated as "D2" detects a 3D structural epitope of MSBI1 which is exclusively accessible under in vivo conditions and is not accessible in Western Blots. In immunofluoresence assays such anti-Rep antibodies detect specifically speckles (cytoplasmatic aggregations) of the Rep protein (often in the periphery of the nuclear membrane.

In certain embodiments the anti-Rep antibodies of groups A, B, C or D; or a combination of anti-Rep antibodies of at least two different groups A, B, C or D are used to determine the kind of Rep protein localisation in a probe and if such a Rep protein localisation correlates with a pathogen function. For instance, if speckles are present. In certain embodiments, i.e., methods or kits of the invention, at least one anti-Rep antibody selected from groups A and B is combined with at least one anti-Rep antibody selected from groups C and D. In particular embodiments, i.e., methods or kits of the invention, an anti-Rep antibody of group A is combined with at least one further anti-Rep antibody selected from the groups B, C, and D. For instance, an anti-Rep antibody of group A may be combined with further anti-Rep antibodies of groups C and D. Such combinations of anti-Rep antibodies of different groups increases the distinctness of the diagnostic assessment, in particular for the diagnosis of MS. These groups A, B, C or D antibodies are preferred for use in the diagnosis of MS.

The following antibodies were deposited with the Deutsche Sammlung für Mikroorganismen and Zellkulturen (DSMZ) [German Collection of Microorganisms and Cell Cultures] on Sep. 28, 2017:

antibody AB01 523-1-1 under DSM ACC3327;
antibody AB02 304-4-1 under DSM ACC3328;
antibody MSBI1 381-6-2 under DSM ACC3329; and
antibody MSBI1 761-5-1 under DSM ACC3330.

Antibody MSBI1 961-2-2 has been deposited with DSMZ on Oct. 6, 2017.

In further embodiments a kit for use in the diagnosis of MS is provided. The kit may include material for detecting anti-Rep antibodies and/or Rep protein together with instructions for use of the materials in assays for the diagnosis of MS. The kit may comprise one or more of the following components: a biomarker according to the invention, i.e. Rep protein and anti-Rep antibodies, e.g. antibodies of Table 1, respectively; a signal generating compound, a solid matrix for attaching a capturing agent, a diluent for the samples, a wash buffer. Signal generating compound refers to a detectable label which is either coupled to an additional binding agent capable of binding to the biomarker of the invention or directly coupled with the biomarker of the invention.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: MSBI1 Rep Protein Purification

A nucleotide acid molecule encoding full-length Rep open reading frame (ORF) identified within the MSBI1 genome is cloned into an expression plasmid (pEXP5-CT, Invitrogen) enabling protein expression based on an *E. coli* high yield cell free in vitro translation system (Expressway™ Cell-Free *E. coli* Expression System, Invitrogen). The synthesized Rep protein having the amino acid sequence of SEQ ID NO:1 within the in vitro translation reaction is denaturated by adding 20 reaction volumes 8 M urea sample buffer pH 8.0 containing 100 mM NaH2PO4, 10 mM Tris HCl, pH 8.0, 5 mM imidazole. The Rep protein is subsequently purified under denaturating conditions (20 mM imidazole for washing and 300 mM imidazole for protein elution) based on a C-terminal His6-tag fused to the Rep protein. Quality of purification is determined by Coomassie protein staining and Western Blotting with anti-Rep protein antibodies. The Rep protein purity is densitometrically calculated and greater 95%. The purified protein is either directly used for ELISA-based serum screening or subjected to SDS-Page followed by transfer blotting onto nitrocellulose membranes for serum incubation of 1D-size-resolved Rep protein membrane stripes.

Example 2: Generation of Serum Master Plates

Serum samples are first aliquoted to reduce sample freeze-thaw cycles. Then, a master plate is established by generating a 1:1 dilution of serum in PBS pH 7.2 stabilized by 0.02% (w/v) sodium azide final concentration in U-shape 96-well plate. This plate is stable for at least 2 months when stored at 4° C. and handled under sterile conditions and is used as template for further serum dilution (1:20 final dilution) prior to the individual screening experiment.

Example 3: Serum Screening by Serum Incubation of 1D-Size-Resolved Rep Protein Membrane Stripes For screening assays based on incubation of 1D-resolved Rep protein membrane stripes with serum, 20 µg purified Rep protein is loaded onto Sigma Tru-PAGE 4-20% precast gels. The walls separating the gel pockets are removed before gel loading to produce one large pocket and a single pocket for a size marker. After the 1D-size resolved SDS-PAGE, the protein is transfer-blotted onto nitrocellulose membranes using a standard wet/tank transfer blot protocol. After that, the protein on the blot membrane (essentially one band of full-length Rep protein at around 40 kDa running height) is visualized with PonceauS to check transfer quality and to prepare the cutting of membrane stripes of 2 mm width and the height of the full 1D-size-resolved membrane. The stripes are then blocked 1 h with each 500 µl serum-free blocking reagent (Genetex Trident universal blocking reagent). After that, serum is characterized based on two different serum dilutions. Serum incubation is performed for 14 h (overnight) at 4° C. on a linear shaking device. After that, the membrane stripes are washed with PBS-T pH7.2 0.1% polysorbate (Tween®) 20 for 3×5 min at room temperature. Detection of Rep-specific bound human IgGs within the sera is done by incubation with an HRP-coupled goat anti-human IgG (H+L) secondary antibody for 1 h at room temperature. After three washes with PBS-T pH7.2 0.1% polysorbate (Tween®) 20 for 3×5 min at room temperature, the stripes of each individual serum incubation are fixed with tape on a plastic foil. The foil is then incubated with ECL substrate (Biorad Clarity) to visualize bound human IgGs on a BioRad WesternBlot detection system. Signals corresponding to the amount of IgGs that specifically bind to the Rep band on the protein membrane are quantified by densitometry.

An example for a result of 1D-size-resolved Rep protein membrane stripes is shown in FIG. 1 and the quantification of seropositive serum/plasma samples is shown in Table 2: Almost 50% of the serum samples gave very strong signals for both dilutions (1:500 and 1:2000) and only 3 of 21 were totally negative. Of the plasma controls, 7 samples gave intermediate signals at 1:500 dilution (some additional one with very low signals) while at 1:2000 dilution only 3 samples gave a very weak signal, while all the others were seronegative. All quantifications sustain the tendency that MS-serum intensities show at least a 30-fold excess of signal when compared to control plasma intensities.

TABLE 2

Quantification of seropositive serum/plasma samples.

| serum dilution | number of seropositive samples | |
| --- | --- | --- |
| 1:2000 | 17 | 3 |
| 1:500 | 21 | 8 |
|  | MS sera | control plasma |

Sera/plasma with detection of Rep-specific human IgGs were counted according to signal intensity for the serum/plasma dilution of 1:500 and 1:2000 for the MS serum pool and the healthy control plasma pool (each 21 in total). Almost 50% of the serum samples gave very strong signals for both dilutions (1:500 and 1:2000) and only 3 of 21 were totally negative. Of the plasma controls, 7 samples gave intermediate signals at 1:500 dilution (some additional one with very low signals) while at 1:2000 dilution only 3 samples gave a very weak signal, while all the others were seronegative. All quantifications sustain the tendency that MS-serum intensities show at least a 30-fold excess of signal when compared to control plasma intensities.

Example 4: Serum Screening by ELISA

An appropriate amount of purified Rep protein (usually between 50 and 200 ng per well) is added to a 1:1 mixture of 8 M urea pH 8.0 and PBS pH 7.2 predisposed into a Maxisorp 96-well ELISA plate (Fisher Scientific). The protein is allowed to bind to the plate matrix for 14 h at 4° C. on a linear shaking device. Then the plate is washed with PBS-T pH 7.2 0.1% polysorbate (Tween®) 20 for 3×5 min at room temperature followed by blocking for at least 14 h at 4° C. with PBS pH 7.2 1% (w/v) BSA finally containing 0.02% sodium azide. After that the serum is added at a dilution of 1:500 and incubation is performed for 6 h at room temperature. After that, the plate is washed with PBS-T pH 7.2 0.1% polysorbate (Tween®) 20 for 3×5 min at room temperature. Detection of Rep-specific bound human IgGs within the sera is done by incubation with an HRP-coupled goat anti-human IgG (H+L) secondary antibody for 1 h at room temperature. After three washes with PBS-T pH 7.2 0.1% polysorbate (Tween®) 20 for 3×5 min at room temperature, 100 µl TMB (3,3',5,5'-tetramethylbenzidine, HRP-sensitive) substrate solution is added per well and incubated for 5 min at room temperature. The reaction is stopped by addition of 100 µl 8M acetic acid/1M sulfuric acid. Signal intensity is quantified on a Perkin Elmer ELISA compatible device by measuring absorbance at 450 nm.

Figure 2:
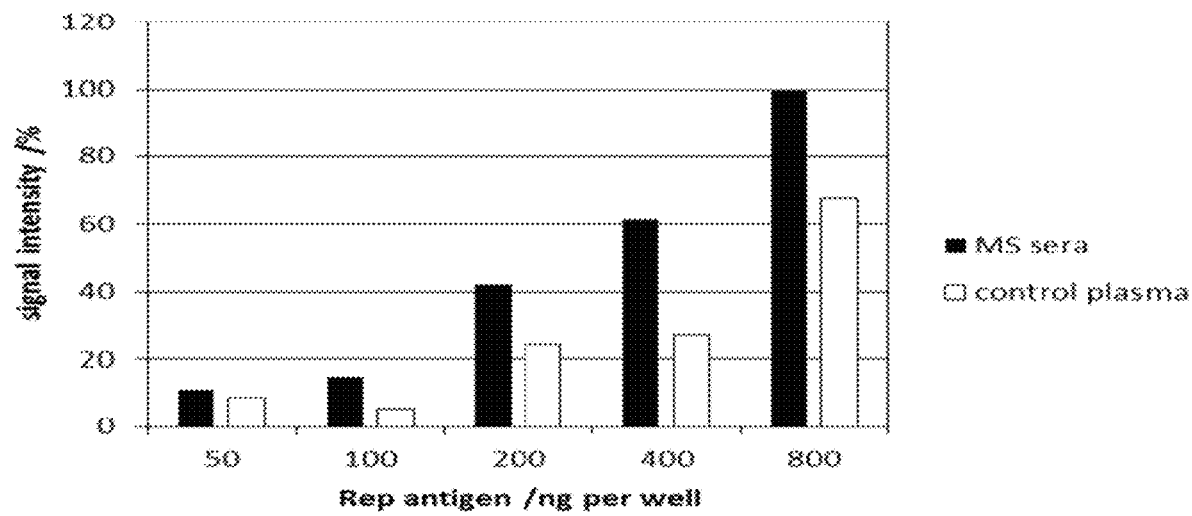
FIG. 2 shows a quantification of Rep-specific sero-responses based on ELISA screening. 50, 100, 200, 400, or 800 ng Rep protein (target antigen) were spotted per 96-well. After blocking and washing the Rep protein antigen was incubated with either a pooled MS serum sample or a pooled control plasma sample at a dilution of 1:500 for 6 h at room temperature (RT). After washing and incubation with a HRP-coupled anti-human IgG HRP secondary antibody and a last washing step, the presence of Rep-bound human IgGs was quantified by TMB substrate reaction and absorbation measurement at 450 nm. Quantification reveals a good correlation of signal intensity and amount of Rep protein (antigen). On average, signal intensity levels of the MS pool exceed intensities of the control pool by at least a factor of 1.9. In general, ELISA based serum screening revealed detectable serum antibodies for at least a serum dilution of 1:1000 (data not shown), so that the titer for this experiment is likely to be greater 1:1000 in the region of 1:2000-1:4000 or even greater after platform optimization.
Figure 3:
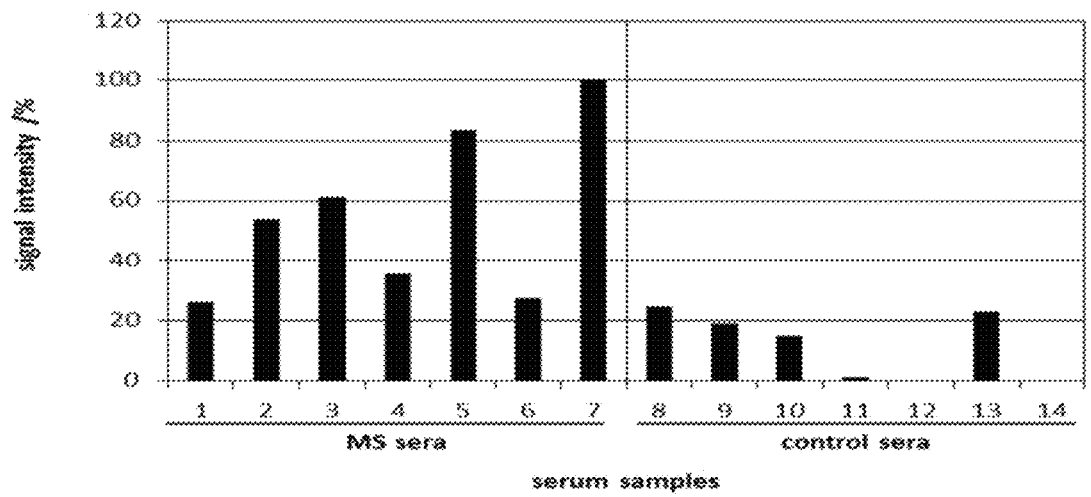
FIG. 3 shows a quantification of Rep-specific sero-responses based on ELISA screening. 200 ng Rep protein (target antigen) were spotted per 96-well. After blocking and washing the Rep protein antigen was incubated with either 7 individual MS sera or 7 individual control sera in duplicates at a dilution of 1:500 for 6 h at room temperature (RT). After washing and incubation with a HRP-coupled anti-human IgG HRP secondary antibody and a last washing step, the presence of Rep-bound human IgGs was quantified by TMB substrate reaction and absorption measurement at 450 nm. Average intensities of the MS samples exceed the average intensity of the control sera by at least a factor of 8 with some MS samples revealing a factor of 10-16 over the average control intensities.

The result of an example of a quantification of Rep-specific sero-responses based on ELISA screening is shown in FIG. 2: Quantification reveals a good correlation of signal intensity and amount of Rep protein (antigen). On average, signal intensity levels of the MS pool exceed intensities of the control pool by at least a factor of 1.9. In general, ELISA based serum screening revealed detectable serum antibodies for at least a serum dilution of 1:1000 (data not shown), so that the titer for this experiment is likely to be greater 1:1000 in the region of 1:2000-1:4000 or even greater after platform optimization.

Example 5: Immunofluorescence Analysis

HEK293TT cells (125.000/well) were cultured for 24 h in immunofluorescence 8-well chambers in DMEM 10% FCS (supplemented with 1× Glutamax (Gibco) and 1× non-essential amino acids (Gibco)) followed by DNA transfection with polyethylenimine (PEI) of either the control plasmid ZsGreen1CI (Clontech) expressing the auto-fluorescence marker protein ZsGreen or the same plasmid bearing the full length MSBI1 Rep ORF at the 3-prime end coding for a ZsGreen-Rep fusion protein. 48 hours after DNA transfection, cells were washed with PBS, fixed for 20 min at RT with PBS 4% PFA at RT and permeabilized with PBS 0.5% Triton X-100 for 10 min at RT on a shaking device. Cells were washed with PBS and blocking was performed with PBS 1% BSA for 45 min at RT. Incubation with the mouse monoclonal anti-Rep antibodies (c.f. Table 1) was performed for 1 h at 37° C. in PBS 1% BSA with 1:500 antibody dilutions (controls lacking primary antibodies were included). Cells were washed three times with PBS followed by incubation with PBS 1% BSA for 15 min at RT. Then, incubation with the secondary antibody (AlexaFluor546 goat anti-mouse, 1:500; DNA marker Hoechst 33342, 1:5.000) was performed for 45 min at RT in PBS 1% BSA. Cells were washed three times with PBS 1% BSA and three times with PBS prior to mounting with cover slips (Dako mounting medium). Immunofluorescence images were taken on a Zeiss Cell Observer (20× objective, fixed exposure time for sample and control dublets).

Figure 4:
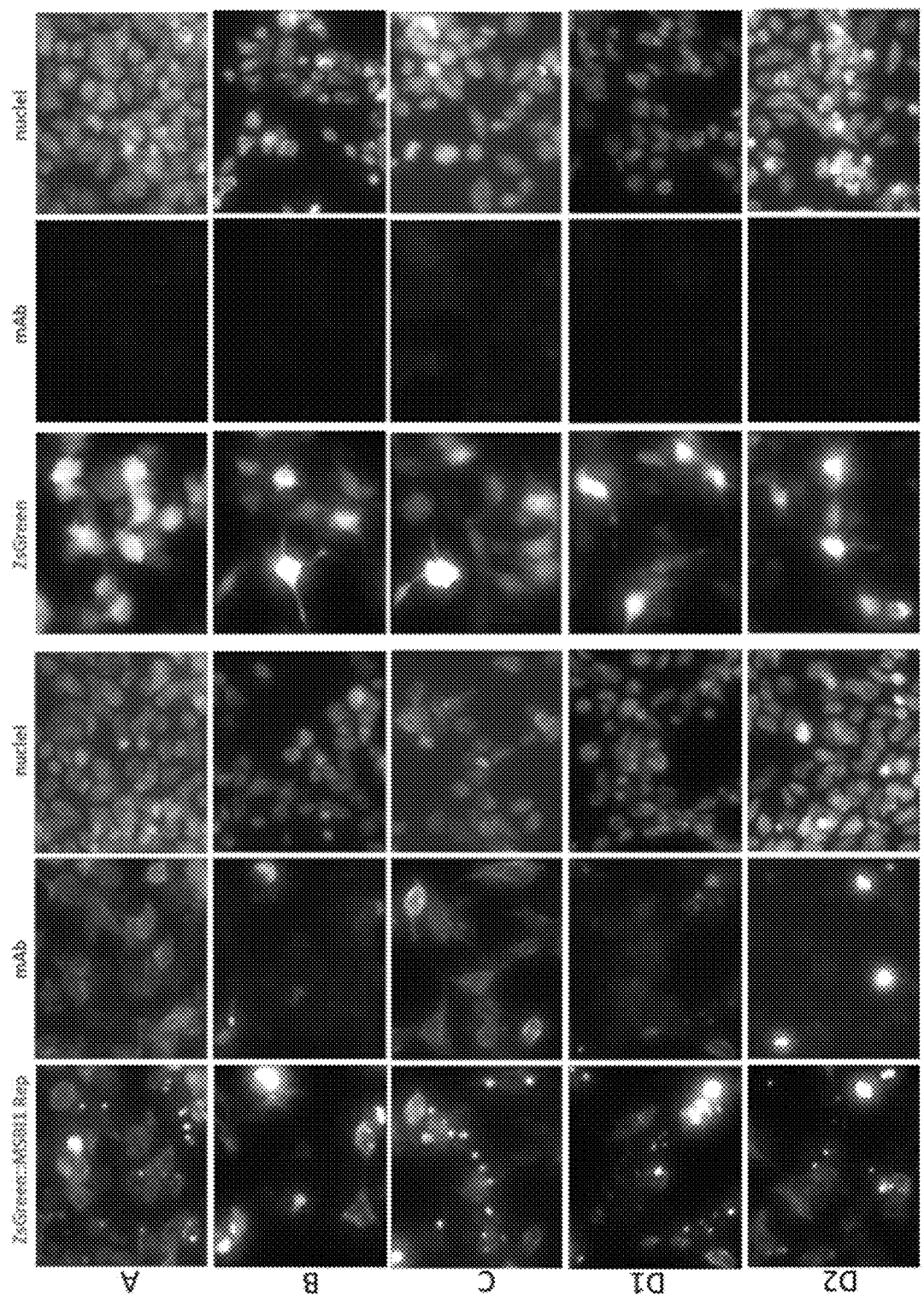
FIGS. 4 to 6 show immunofluorescence image data obtained by employment of anti-Rep antibodies A, B, C, D1 and D2 which are designated on the y-coordinates.

The immunofluorescence images (FIG. 4) show that antibody treatment with group A and C antibodies leads to specific detection of cytoplam+nuclear membrane (+nucleus)-localized target protein without detection of aggregates. In contrast, group B and D antibodies show specific colocalization with speckled protein and no to weak levels of cytoplasmatic signals. The control incubation of the antibodies on the ZsGreen fusion protein alone did not result in significant signal detection (same exposition times used for visualization of the antibody signals).

Example 6: Immunofluorescence Analysis

HEK293TT cells (125.000/well) were cultured for 24 h in immunofluorescence 8-well chambers in DMEM 10% FCS (supplemented with 1× Glutamax (Gibco) and 1× non-essential amino acids (Gibco)) followed by DNA transfection with polyethylenimine (PEI) of either the control plasmid ZsGreen1CI (Clontech) expressing the auto-fluorescence marker protein ZsGreen or the same plasmid bearing the full length CMI1 Rep ORF at the 3-prime end coding for a ZsGreen-Rep fusion protein. 48 hours after DNA transfection, cells were washed with PBS, fixed for 20 min at RT with PBS 4% PFA at RT and permeabilized with PBS 0.5% Triton X-100 for 10 min at RT on a shaking device. Cells were washed with PBS and blocking was performed with PBS 1% BSA for 45 min at RT. Incubation with the mouse monoclonal anti-Rep antibodies (Table 1) was performed for 1 h at 37° C. in PBS 1% BSA with 1:500 antibody dilutions (controls lacking primary antibodies were included). Cells were washed three times with PBS followed by incubation with PBS 1% BSA for 15 min at RT. Then, incubation with the secondary antibody (AlexaFluor546 goat anti-mouse, 1:500; DNA marker Hoechst 33342, 1:5.000) was performed for 45 min at RT in PBS 1% BSA. Cells were washed three times with PBS 1% BSA and three times with PBS prior to mounting with cover slips (Dako mounting medium). Immunofluorescence images were taken on a Zeiss Cell Observer (20× objective, fixed exposure time for sample and control dublets).

Figure 5:
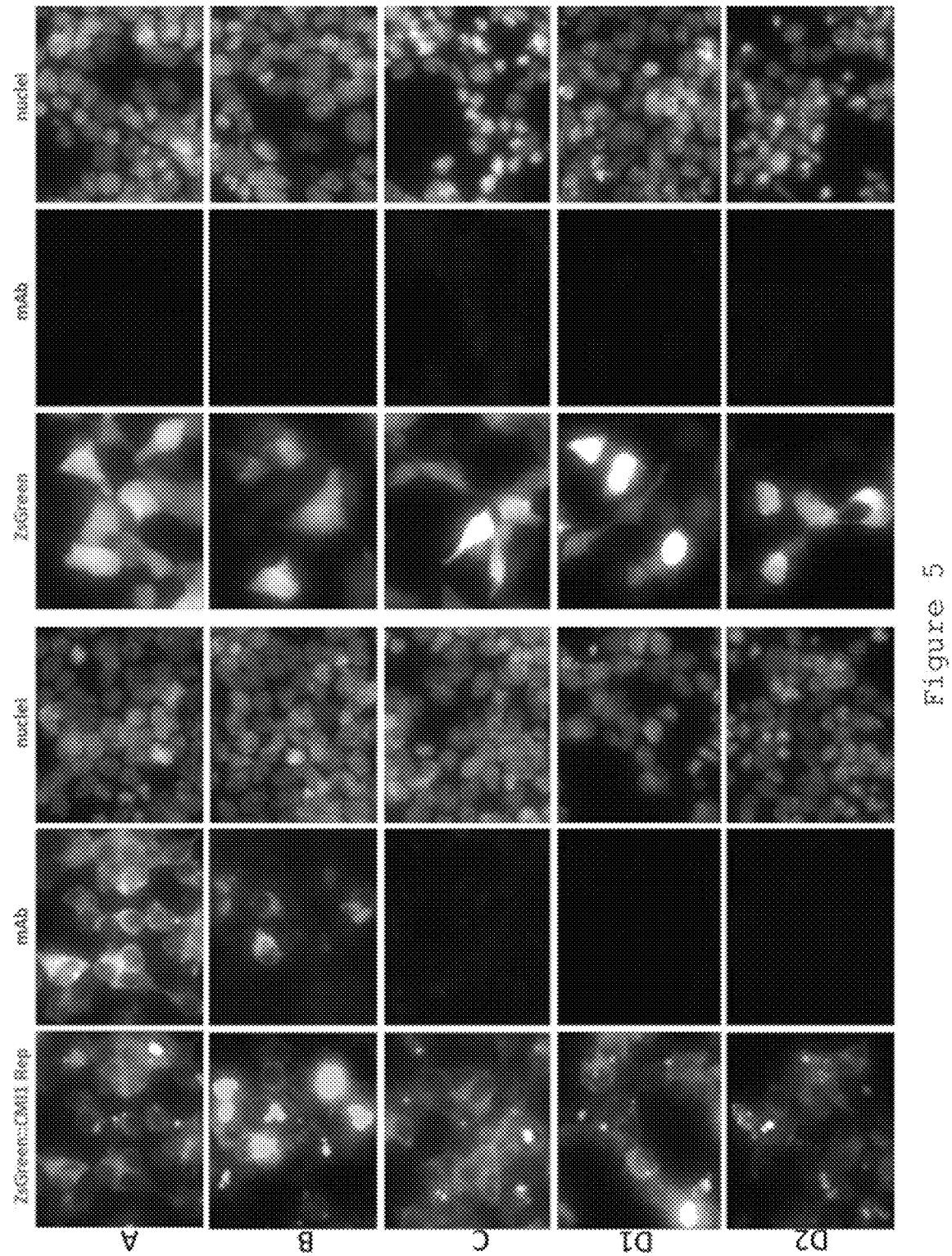

The immunofluorescence images (FIG. 5) show that while the group A antibody specifically detects cytoplasm+nuclear membrane (+nucleus)-localized target protein without detection of aggregates, group B antibody detects speckled target protein with a minimal background of cytoplasmic localized target protein. The MSBI1-specific antibodies of group C and D do not lead to specific detection of signals. Both antibodies D1 and D2 belong to the "D" group but have slightly different epitope recognition.

Example 7: Immunofluorescence Analysis

HEK293TT cells (125.000/well) were cultured for 24 h in immunofluorescence 8-well chambers in DMEM 10% FCS (supplemented with 1× Glutamax (Gibco) and 1× non-essential amino acids (Gibco)) followed by DNA transfection with polyethylenimine (PEI) of either the control plasmid pcDNA3.1(−) (Invitrogen) or the same plasmid expressing a codonoptimized variant of the full length MSBI1 Rep ORF (SEQ ID. No.: 13). 48 hours after DNA transfection, cells were washed with PBS, fixed for 20 min at RT with PBS 4% PFA at RT and permeabilized with PBS 0.5% Triton X-100 for 10 min at RT on a shaking device. Cells were washed with PBS and blocking was performed with PBS 1% BSA for 45 min at RT. Incubation with the mouse monoclonal anti-Rep antibodies (Table 1) was performed for 1 h at 37° C. in PBS 1% BSA with 1:500 antibody dilutions (controls lacking primary antibodies were included). Cells were washed three times with PBS followed by incubation with PBS 1% BSA for 15 min at RT. Then, incubation with the secondary antibody (AlexaFluor488 goat anti-mouse, 1:500; DNA marker Hoechst 33342, 1:5.000) was performed for 45 min at RT in PBS 1% BSA. Cells were washed three times with PBS 1% BSA and three times with PBS prior to mounting with cover slips (Dako mounting medium). Immunofluorescence images were taken on a Zeiss Cell Observer (20× objective, fixed exposure time for sample and control dublets).

Figure 6:
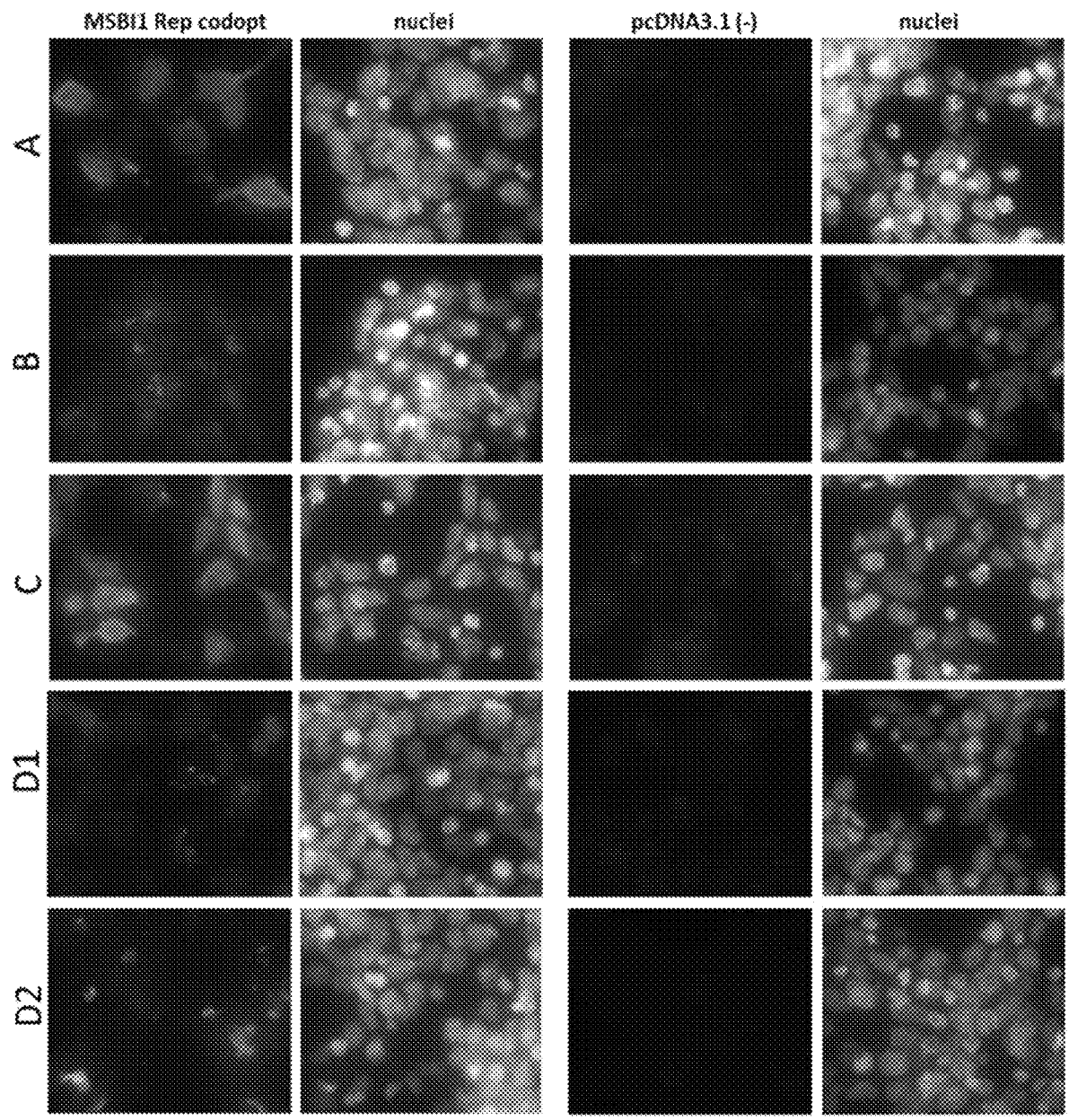

The immunofluorescence images (FIG. 6) show that antibody treatment with group A and C antibodies leads to specific detection of cytoplam+nuclear membrane (+nucleus)-localized target protein without detection of aggregates. In contrast, group B and D antibodies show specific colocalization with speckled protein and no to weak levels of cytoplasmatic signals. The control incubation of the antibodies on the ZsGreen fusion protein alone did not result in significant signal detection (same exposition times used for visualization of the antibody signals).

Example 8: Western Blot Analysis

HEK293TT (1.5 Mio/6-well) were cultured for 24 h in 6-well cell culture plates in DMEM 10% FCS (supplemented with 1× Glutamax (Gibco) and 1× non-essential amino acids (Gibco)) followed by DNA transfection with polyethylenimine (PEI) of ZsGreen1CI plasmids coding for overexpression of the full length MSBI1, CMI1 or MSBI2 Rep protein as fusion protein with an N-terminal ZsGreen tag. 48 hours after DNA transfection, cells were washed with PBS, detached by trypsination, washed again with PBS and lysed in SDS-PAGE Lämmli buffer (boil for 5 min at 98° C.). The samples were loaded onto precast 12.5% SDS-PAGE gels with one large pocket. After transferblot, each two stripes of the membrane were cut for individual incubation of the stripes with the different mouse monoclonal antibodies of Table 1 (1:1000 dilution in PBS 5% skim milk) after blocking with PBS 5% skim milk. The stripes were washed three times with PBS 0.1% polysorbate (Tween®) 20 and incubated with the HRP-coupled anti-mouse secondary antibody allowing Westernblot analysis of antibodies detecting the different ZsGreen-Rep fusion proteins on a Biorad ChemiDoc device. Positive control detection was performed based on incubation with a ZsGreen antibody (OriGene, 1:2000)

Figure 7:
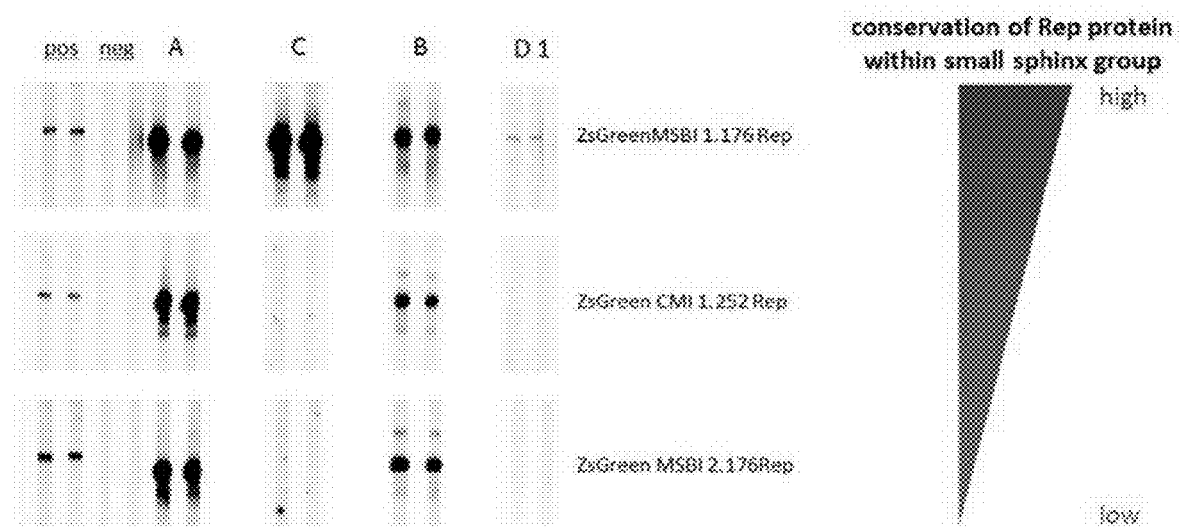
FIG. 7 shows a Western Blot Analysis, wherein A, B, C and D1 designate the groups of the employed anti-Rep antibodies.

FIG. 7 shows while antibodies of the groups A and B specifically detect all three Rep fusion proteins, including the CMI1 and MSBI2 Rep fusion proteins in addition to the MSBI1 Rep fusion protein, the MSBI1-specific antibodies of group C and D exclusively detect the MSBI1 Rep fusion protein. Antibody D2 is WB-negative most likely due to detection of a 3D structure epitope, which is not prevailed under denaturing condition in SDS-PAGE and was not tested here.

Sequence Summary

| SEQ ID NO | SEQUENCE |
|---|---|
| 1 | Amino acid sequence of Rep protein encoded by MSBI1.176<br>MSDLIVKDNALMNASYNLALVEQRLILLAIIEARETGKGINANDPLTVHASSYINQFN<br>VERHTAYQALKDACKDLFARQFSYQEKRERGRINITSRWVSQIGYMDDT<br>ATVEIIFAPAVVPLITRLEEQFTQYDIEQISGLSSAYAVRMYELLICWRSTGKTPII<br>ELDEFRKRIGVLDTEYTRTDNLKMRVIELALKQINEHTDITASYEQHKKGRVIT<br>GFSFKFKHKKQNSDKTPKNSDSSPRIVKHSQIPTNIVKQPENAKMSDLEHRASR<br>VTGEIMRNRLSDRFKQGDESAIDMMKRIQSEIITDAIADQWESKLEEFGVVF |
| 2 | Amino acid sequence of Rep peptide fragment<br>EARETGKGINANDPLTVH |
| 3 | Amino acid sequence of Rep peptide fragment<br>KQINEHTDITASYEQHKKGRT |
| 4 | His-Tag (with two neutral stuffer amino acids)<br>GAHHHHHH |
| 5 | T7-Tag<br>MASMTGGQQMG |
| 6 | FLAG-Tag<br>DYKDDDDK |
| 7 | Strep-II-Tag<br>WSHPQFEK |
| 8 | Amino acid sequence of Rep protein encoded by MSBI2.176<br>MSKLVVKDNALMNASYNLDLVEQRLILLAIIEARESGKGINANDPLTVHA<br>ESYINQFGVHRVTAYQALKDACDNLFARQFSYQSKSEKGNIQNHRSRWVS<br>EIIYIDTEATVKIIFAPAIVPLITRLEEQFTKYDIEQISDLSSAYAIRLY<br>ELLICWRSTGKTPIIGLGEFRNRVGVLDSEYHRIAHLKERVIEHSIKQIN<br>EHTDITATYEQHKKGRTITGFSFKFKQKKPKQAEIATETPKTATNDPDTT<br>KPLTEPQIAKYSMILCKLGSISDLSNFPDYPAFANWIGNILRNPEKADEQ<br>IAKRIFTALKTETDYSKKN |
| 9 | MSBI.1 specific epitope<br>NRLSDRF |
| 10 | Amino acid sequence of Rep protein encoded by CMI1.252<br>MSDLIVKDNALMNASYNLALVEQRLILLAILEARETGKGINANDPLTVHASSYI<br>NQFNVERHTAYQALKDACKDLFARQFSYQEKRERGRINITSRWVSQIGYMDDT<br>ATVEIIFAPAVVPLITRLEEQFTQYDIEQISELSSAYAVRLYELLICWRSTGKTPII |

| SEQ ID NO | SEQUENCE |
|---|---|
| | DLTEFRKRLGVLDTEYTRTDNLKMRVIELGLKQINEHTDITASYEQHKKGRTIT<br>GFSFKFKQKKKTGAEMPKNSDSSPHIEKPSQIPANIAKQPENAKKDDLGHRASK<br>ITGLIMSNGLADRFKRGDESVIDMMKRIKEEITTDTTADQWENKLEEFGVIFQS |
| 11 | Amino acid sequence of Rep protein encoded by CMI2.214<br>MSDLIVKDNALMNASYNLDLVEQRLILLAILEARETGKGINANDPLTVHAESYI<br>NQFGVARQTAYQALKDACKDLFARQFSYQEKRERGRANITSRWVSQIAYIDET<br>ATVEVIFAPAVVPLITRLEEQFTQYDIEQISGLSSAYAVRLYELLICWRSTGKTPV<br>IELAEFRKRLGVLNDEYTRSDNFKKWIIENPIKQINEHTDITASYEQHKKGRTIT<br>GFSFKFKQKKKTEPETPKNSDSSQRIEKPSQIPANIVKQPENANLSDLQHRASKI<br>TGLIMSNRLSDRFKQGDESIMQMMARIQSEITTDSIADQWQSKLEEFGVVF |
| 12 | Amino acid sequence of Rep protein encoded by CMI3.168<br>MSDLIVKDNALMNASYNLALVEQRLILLAILEARETGKGINANDPLTVHASSYI<br>NQFNVERHTAYQALKDACKDLFARQFSYQEKRERGRANITSRWVSQIAYIDET<br>ATVEVIFAPAVVPLITRLEEQFTQYDIEQISGLSSAYAVRLYELLICWRTTGKTP<br>VLDLTEFRKRLGVLDTEYTRTDNLKMRVIEQSLKQINKHTDITASYEQHKKGR<br>TITGFSFKFQKKKTEPETPKNNDSGVSKPKTVEIPAEVVKQPKNTNLSDLEKR<br>VRMITGAIAKNNLASRFQHGNESPLDMMKRIQSEITSDETADLWQNKLESMGV<br>VF |
| 13 | DNA sequence MSBI1 Rep codon-optimized<br>ATGAGCGACCTGATCGTGAAAGACAATGCCCTGATGAACGCCTCCTACAAC<br>CTGGCACTGGTCGAACAGAGACTGATTCTGCTGGCTATCATCGAGGCAAGG<br>GAGACCGGCAAGGGCATCAACGCCAATGACCCCCTGACAGTGCACGCCAG<br>CTCCTACATCAACCAGTTTAATGTGGAGCGCCACACCGCCTATCAGGCCCT<br>GAAGGACGCCTGCAAGGATCTGTTTGCCCGGCAGTTCAGCTACCAGGAGAA<br>GCGGGAGAGAGGCAGGATCAACATCACAAGCAGATGGGTGTCCCAGATCG<br>GCTATATGGACGATACCGCCACAGTGGAGATCATCTTTGCACCAGCAGTGG<br>TGCCTCTGATCACCAGGCTGGAGGAGCAGTTCACACAGTACGACATCGAGC<br>AGATCTCCGGACTGTCTAGCGCCTACGCCGTGCGCATGTATGAACTGCTGA<br>TCTGTTGGCGGTCTACCGGCAAGACACCTATCATCGAGCTGGATGAGTTCC<br>GCAAGCGGATCGGCGTGCTGGACACCGAGTACACCAGAACAGATAACCTG<br>AAGATGAGAGTGATCGAGCTGGCCCTGAAGCAGATCAATGAGCACACCGA<br>TATCACAGCCTCTTATGAGCAGCACAAGAAGGGCCGCGTGATCACCGGCTT<br>CAGCTTTAAGTTCAAGCACAAGCAGAACTCTGACAAGACACCAAAGA<br>ATAGCGATTCCTCTCCCCGGATCGTGAAGCACAGCCAGATCCCTACCAACA<br>TCGTGAAGCAGCCAGAGAATGCCAAGATGTCCGACCTGGAGCACAGGGCA<br>TCTAGGGTGACAGGCGAGATCATGAGAAATAGGCTGAGCGATCGGTTCAA<br>GCAGGGCGACGAGTCCGCCATCGATATGATGAAGAGAATCCAGTCCGAGA<br>TCATCACCGACGCCATCGCCGATCAGTGGGAATCTAAACTGGAAGAGTTTG<br>GAGTCGTGTTTGGAGCACATCACCATCATCATCACTGA |
| 14 | Protein sequence MSBI1 Rep codon-optimized<br>MSDLIVKDNALMNASYNLALVEQRLILLAIIEARETGKGINANDPLTVHASSYI<br>NQFNVERHTAYQALKDACKDLFARQFSYQEKRERGRINITSRWVSQIGYMDDT<br>ATVEIIFAPAVVPLITRLEEQFTQYDIEQISGLSSAYAVRMYELLICWRSTGKTPII<br>ELDEFRKRIGVLDTEYTRTDNLKMRVIELALKQINEHTDITASYEQHKKGRVIT<br>GFSFKFKHKKQNSDKTPKNSDSSPRIVKHSQIPTNIVKQPENAKMSDLEHRASR<br>VTGEIMRNRLSDRFKQGDESAIDMMKRIQSEIITDAIADQWESKLEEFGVVFGA |
| 15 | DNA sequence MSBI1 Rep wild-type<br>ATGAGCGATTTAATAGTAAAAGATAACGCCCTAATGAATGCTAGTTATAAC<br>TTAGCTTTGGTTGAACAGAGGTTAATTCTATTAGCAATCATAGAAGCGAGA<br>GAAACAGGCAAAGGGATTAATGCCAATGATCCTTTAACAGTTCATGCAAGT<br>AGCTATATCAATCAATTTAACGTAGAAAGGCATACGGCATATCAAGCCCTC<br>AAAGATGCTTGTAAAGACTTGTTTGCCCGTCAATTCAGTTACCAAGAAAAG<br>CGAGAACGAGGACGAATTAATATTACAAGTCGATGGGTTTCGCAAATTGGC<br>TATATGGACGATACAGCAACCGTTGAGATTATTTTTGCCCCTGCGGTTGTTC<br>CTCTGATTACACGGCTAGAGGAACAGTTCACCCAGTACGATATTGAGCAAA<br>TTAGCGGTTTATCGAGTGCATATGCTGTTCGTATGTACGAACTGCTGATTTG<br>TTGGCGTAGCACAGGCAAAACACCAATTATTGAGCTAGACGAGTTTAGAAA<br>GCGAATAGGTGTTTTAGATACTGAATACACTAGAACAGATAATTTAAAGAT<br>GCGAGTTATTGAATTAGCCCTAAAACAAATCAACGAACATACAGACATCAC<br>AGCAAGCTATGAACAACACAAAAAAGGGCGAGTGATTACAGGATTCTCATT<br>CAAGTTTAAGCACAAGAAACAAAACAGCGATAAAACGCCAAAAAATAGCG<br>ATTCTAGCCCACGTATCGTAAAACATAGTCAAATCCCTCCAACATTGTAAA<br>ACAGCCTGAAAACGCCAAAATGAGCGATTTAGAACATAGAGCGAGCCGTG<br>TTACAGGGGAAATAATGCGAAATCGTCTGTCAGATCGGTTTAAACAAGGCG<br>ATGAATCAGCAATCGACATGATGAAACGTATTCAAAGTGAAATAATAACCG<br>ATGCAATAGCAGACCAGTGGGAAAGCAAACTGGAGGAGTTTGGCGTGGTTT<br>TTTAG |

REFERENCES

Funk, M., et al. (2014). "Isolation of protein-associated circular DNA from healthy cattle serum". Genome Announc 2(4)

Giraldo, R., et al. (2011). "RepA-WH1 prionoid: a synthetic amyloid proteinopathy in a minimalist host." Prion 5(2): 60-64

Gunst, K., et al. (2014). "Isolation of bacterial plasmid-related replication-associated cirular DNA from a serum sample of a multiple sclerosis patient." Genome Announc 2(4).

Lamberto, I., et al. (2014). "Mycovirus-like DNA virus sequences from cattle serum and human brain and serum samples from multiple sclerosis patients." Genome Announc 2(4).

Manuelidis L., 2011. "Nuclease resistant circular DNAs co-purify with infectivity in scrapie and CJD". J. Neurovirol. 17:131-145.

Torreira, E., et al. (2015). "Amyloidogenesis of bacterial prionoid RepA-WH1 recaptiulates dimer to monomer transitions of RepA in DNA replication initiation." Structure 23(1):183-189

Whitley, C., et al. (2014). "Novel replication-competent cirulara DNA molecules from healthy cattle serum and milk and multiple sclerosis-affected human brain tissue." Genome Announc 2(4).

The invention is further described by the following numbered paragraphs:

1. A DNA-replication-associated (Rep) protein for use in the diagnosis of multiple sclerosis (MS), wherein
    (a) an at least 2-fold increased amount of Rep protein or fragments thereof in a sample from a subject as compared to an amount in a control sample; or
    an at least 2-fold increased amount of anti-Rep antibodies in a sample from a subject as compared to an amount in a control sample
    correlates with a diagnosis of MS; and
    (b) the Rep protein comprises
        (i) an amino acid sequence as depicted in SEQ ID NO:1;
        (ii) a fragment of SEQ ID NO:1 which is capable of binding an anti-Rep antibody specific for a protein having the amino acid sequence of SEQ ID NO 1; or
        (iii) an amino acid sequence having a 90% or more homology to the amino acid sequence of (i) or (ii) and is capable of binding an anti-Rep antibody specific for a protein having an amino acid sequence of SEQ ID NO:1.

2. The Rep protein of paragraph 1, wherein the fragment of SEQ ID NO:1 comprises an epitope within the amino acid sequence consisting of amino acids 1 to 229 of SEQ ID NO:1.

3. The Rep protein of paragraph 1 or 2, wherein an increased amount of Rep protein or fragments thereof or anti-Rep antibodies of at least 5-fold as compared to a control sample indicates MS.

4. The Rep-protein of paragraph 1, wherein the protein is encoded by a polynucleotide acid as depicted in SEQ ID NO:13.

5. An anti-Rep antibody selected from the group consisting of antibody AB01 523-1-1 (DSM ACC3327), antibody AB02 304-4-1 (DSM ACC3328), antibody MSBI1 381-6-2 (DSM ACC3329), antibody MSBI1 761-5-1 (DSM ACC3330) and antibody MSBI1 961-2-2.

6. Use of an anti-Rep antibody of paragraph 5 in a method of any one of paragraphs 1 to 4.

7. A method of diagnosing MS in a subject comprising the steps of
    (a) incubating a sample from a subject with Rep protein as defined in (b) of paragraph 1;
    (b) detecting the amount of antibodies in the sample from the subject forming an immunological complex with Rep protein; and
    (c) correlating an at least 2-fold increased amount of antibody bound to Rep protein in the sample from the subject, as compared to an amount in a control sample, with a diagnosis of MS.

8. The method of paragraph 7, wherein in step (a) the Rep protein is immobilized followed by incubating the immobilized Rep protein with the sample from the subject.

9. The method of paragraph 7, wherein in step (a) the Rep protein is expressed in cells followed by incubating the cells with the sample from the subject.

10. The method of paragraph 8 or 9, wherein in step (b) the amount of antibodies forming an immunological complex with Rep protein is quantified by a detecting binding agent coupled to a signal generating compound.

11. The method of paragraph 7, wherein in step (a) the antibodies in the sample from the subject are immobilized followed by incubating with a defined amount of Rep protein.

12. The method of any one of paragraphs 7 to 11, wherein the sample from the subject is a serum or a plasma sample.

13. A method of diagnosing MS in a patient comprising the steps of
    (a) detecting the amount of Rep protein in a sample from a subject by anti-Rep antibodies that bind to an epitope comprised by SEQ ID NO:2 or SEQ ID NO:3, and
    (b) correlating an at least 2-fold increased amount of Rep protein detected in the sample from a subject in step (a) as compared to an amount in a control sample with a diagnosis of MS.

14. The method of paragraph 13, wherein the antibody specific for Rep protein binds to an epitope that is within an amino acid sequence selected from the group consisting of amino acids from 1 to 136, from 137 to 229 and from 230 to 324 of SEQ ID NO:1.

15. The method of paragraph 13 or 14, wherein the sample from a subject is selected from the group consisting of a serum sample, plasma sample or tissue sample.

16. A kit for use in the diagnosis of MS comprising:
    (a) a Rep protein, wherein the Rep protein comprises:
        (i) an amino acid sequence as depicted in SEQ ID NO:1;
        (ii) a fragment of SEQ ID NO:1 which is capable of binding an anti-Rep antibody with specificity for a protein having the amino acid sequence of SEQ ID NO: 1; or
        (iii) an amino acid sequence having a 90% or more homology to the amino acid sequence of (i) or (ii) and is capable of binding an anti-Rep antibody with specificity for a protein having the amino acid sequence of SEQ ID NO:1,
    (b) an anti-human antibody coupled to a detectable label and capable of binding to anti-Rep antibody with specificity for a protein having the amino acid sequence of SEQ ID NO: 1, and
    (c) a solid matrix suitable for immobilizing a Rep protein according to (a) or anti-Rep antibodies with specificity for a protein having the amino acid sequence of SEQ ID NO: 1 suspected in a serum or plasma sample.

17. The kit according to paragraph 16 for use in an assay selected from the group consisting of enzyme-linked immunosorbent assay (ELISA), radioimmunoassay (RIA), enzyme immune assay (EIA), fluorescence immunoassay (FIA), luminescence immunoassay (LIA) and strip assay.

Having thus described in detail preferred embodiments of the present invention, it is to be understood that the inven- tion defined by the above paragraphs is not to be limited to particular details set forth in the above description as many apparent variations thereof are possible without departing from the spirit or scope of the present invention.

What is claimed is:

1. A method of diagnosing multiple sclerosis (MS) in a human patient comprising the steps of
   (a) incubating a sample from the human patient selected from the group consisting of blood, serum and plasma with a DNA-replication-associated (Rep) protein comprising,
   (i) the amino acid sequence as depicted in SEQ ID NOS: 1 or 14; or
   (ii) a fragment of the amino acid sequence as depicted in SEQ ID NO: 1 and the fragment consists of the amino acid selected from the group consisting of the amino acids 1 to 136 or 137 to 229 of SEQ ID NO:1 and SEQ ID NOS: 2, 3 or 9;
   (b) detecting the amount of antibodies in the sample from the human patient forming an immunological complex with the Rep protein;
   (c) determining the extent of difference in the amount of antibodies present in the sample from the human patient and a control sample taken from a healthy individual who has not been diagnosed for MS; and
   (d) diagnosing MS, when the amount of antibodies bound to Rep protein in the sample from the human patient is at least 2-fold increased, as compared to the amount in the control sample.

2. The method of claim 1, wherein the protein is encoded by a polynucleotide acid as depicted in SEQ ID NO:13.

3. The method of claim 1, wherein in step (a) the Rep protein is immobilized followed by incubating the immobilized Rep protein with the sample from the subject.

4. The method of claim 1, wherein in step (a) the Rep protein is expressed in cells followed by incubating the cells with the sample from the subject.

5. The method of claim 3, wherein in step (b) the amount of antibodies forming an immunological complex with the immobilized Rep protein is quantified by a detecting binding agent coupled to a signal generating compound.

6. The method of claim 4, wherein in step (b) the amount of antibodies forming an immunological complex with Rep protein is quantified by a detecting binding agent coupled to a signal generating compound.

7. The method of claim 1, wherein in step (a) the antibodies in the sample from the subject are immobilized followed by incubating with a defined amount of Rep protein.

8. The method of claim 5, wherein in step (a) the Rep protein is bound to a solid support and in step (b) the detecting binding agent is an anti-human antibody coupled to a signal generating compound.

9. The method of claim 8, wherein the signal generating compound is selected from the group consisting of enzymatic, fluorescent, chemiluminescent, radioactive and dye molecules.

10. The method of claim 9, wherein the signal generating compound is horseradish peroxidase.

11. The method of claim 4, wherein the Rep protein expressed in cells comprises the amino acid sequence as depicted in SEQ ID NO: 14.

12. The method of claim 11, wherein the Rep protein is encoded by the polynucleotide acid as depicted in SEQ ID NO: 13.

* * * * *

SEQUENCE LISTING

<160> NUMBER OF SEQ ID NOS: 15

<210> SEQ ID NO 1
<211> LENGTH: 324
<212> TYPE: PRT
<213> ORGANISM: artificial sequence
<220> FEATURE:
<223> OTHER INFORMATION: MSBI1 Rep protein

<400> SEQUENCE: 1

```
Met Ser Asp Leu Ile Val Lys Asp Asn Ala Leu Met Asn Ala Ser Tyr
1               5                   10                  15

Asn Leu Ala Leu Val Glu Gln Arg Leu Ile Leu Ala Ile Ile Glu
            20                  25                  30

Ala Arg Glu Thr Gly Lys Gly Ile Asn Ala Asn Asp Pro Leu Thr Val
        35                  40                  45

His Ala Ser Ser Tyr Ile Asn Gln Phe Asn Val Glu Arg His Thr Ala
    50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ile Asn Ile Thr Ser Arg
                85                  90                  95

Trp Val Ser Gln Ile Gly Tyr Met Asp Asp Thr Ala Thr Val Glu Ile
            100                 105                 110

Ile Phe Ala Pro Ala Val Val Pro Leu Ile Thr Arg Leu Glu Glu Gln
        115                 120                 125

Phe Thr Gln Tyr Asp Ile Glu Gln Ile Ser Gly Leu Ser Ser Ala Tyr
    130                 135                 140

Ala Val Arg Met Tyr Glu Leu Leu Ile Cys Trp Arg Ser Thr Gly Lys
145                 150                 155                 160

Thr Pro Ile Ile Glu Leu Asp Glu Phe Arg Lys Arg Ile Gly Val Leu
                165                 170                 175

Asp Thr Glu Tyr Thr Arg Thr Asp Asn Leu Lys Met Arg Val Ile Glu
            180                 185                 190

Leu Ala Leu Lys Gln Ile Asn Glu His Thr Asp Ile Thr Ala Ser Tyr
        195                 200                 205

Glu Gln His Lys Lys Gly Arg Val Ile Thr Gly Phe Ser Phe Lys Phe
    210                 215                 220

Lys His Lys Lys Gln Asn Ser Asp Lys Thr Pro Lys Asn Ser Asp Ser
225                 230                 235                 240

Ser Pro Arg Ile Val Lys His Ser Gln Ile Pro Thr Asn Ile Val Lys
                245                 250                 255

Gln Pro Glu Asn Ala Lys Met Ser Asp Leu Glu His Arg Ala Ser Arg
            260                 265                 270

Val Thr Gly Glu Ile Met Arg Asn Arg Leu Ser Asp Arg Phe Lys Gln
        275                 280                 285

Gly Asp Glu Ser Ala Ile Asp Met Met Lys Arg Ile Gln Ser Glu Ile
    290                 295                 300

Ile Thr Asp Ala Ile Ala Asp Gln Trp Glu Ser Lys Leu Glu Glu Phe
305                 310                 315                 320

Gly Val Val Phe
```

<210> SEQ ID NO 2

```
<211> LENGTH: 18
<212> TYPE: PRT
<213> ORGANISM: artificial sequence
<220> FEATURE:
<223> OTHER INFORMATION: Rep peptide

<400> SEQUENCE: 2

Glu Ala Arg Glu Thr Gly Lys Gly Ile Asn Ala Asn Asp Pro Leu Thr
1               5                   10                  15

Val His

<210> SEQ ID NO 3
<211> LENGTH: 20
<212> TYPE: PRT
<213> ORGANISM: artificial sequence
<220> FEATURE:
<223> OTHER INFORMATION: Rep peptide

<400> SEQUENCE: 3

Lys Gln Ile Asn Glu His Thr Asp Ile Thr Ala Ser Tyr Glu His Lys
1               5                   10                  15

Lys Gly Arg Thr
            20

<210> SEQ ID NO 4
<211> LENGTH: 8
<212> TYPE: PRT
<213> ORGANISM: artificial sequence
<220> FEATURE:
<223> OTHER INFORMATION: His tag

<400> SEQUENCE: 4

Gly Ala His His His His His His
1               5

<210> SEQ ID NO 5
<211> LENGTH: 11
<212> TYPE: PRT
<213> ORGANISM: artificial sequence
<220> FEATURE:
<223> OTHER INFORMATION: T7 tag

<400> SEQUENCE: 5

Met Ala Ser Met Thr Gly Gly Gln Gln Met Gly
1               5                   10

<210> SEQ ID NO 6
<211> LENGTH: 8
<212> TYPE: PRT
<213> ORGANISM: artificial sequence
<220> FEATURE:
<223> OTHER INFORMATION: FLAG tag

<400> SEQUENCE: 6

Asp Tyr Lys Asp Asp Asp Asp Lys
1               5

<210> SEQ ID NO 7
<211> LENGTH: 8
<212> TYPE: PRT
<213> ORGANISM: artificial sequence
<220> FEATURE:
<223> OTHER INFORMATION: Trep II tag

<400> SEQUENCE: 7

Trp Ser His Pro Gln Phe Glu Lys
```

<210> SEQ ID NO 8
<211> LENGTH: 319
<212> TYPE: PRT
<213> ORGANISM: artificial sequence
<220> FEATURE:
<223> OTHER INFORMATION: MSBI2.176

<400> SEQUENCE: 8

Met Ser Lys Leu Val Val Lys Asp Asn Ala Leu Met Asn Ala Ser Tyr
1               5                   10                  15

Asn Leu Asp Leu Val Glu Gln Arg Leu Ile Leu Leu Ala Ile Ile Glu
            20                  25                  30

Ala Arg Glu Ser Gly Lys Gly Ile Asn Ala Asn Asp Pro Leu Thr Val
        35                  40                  45

His Ala Glu Ser Tyr Ile Asn Gln Phe Gly Val His Arg Val Thr Ala
    50                  55                  60

Tyr Gln Ala Leu Lys Asp Ala Cys Asp Asn Leu Phe Ala Arg Gln Phe
65                  70                  75                  80

Ser Tyr Gln Ser Lys Ser Glu Lys Gly Asn Ile Gln Asn His Arg Ser
                85                  90                  95

Arg Trp Val Ser Glu Ile Ile Tyr Ile Asp Thr Glu Ala Thr Val Lys
            100                 105                 110

Ile Ile Phe Ala Pro Ala Ile Val Pro Leu Ile Thr Arg Leu Glu Glu
        115                 120                 125

Gln Phe Thr Lys Tyr Asp Ile Glu Gln Ile Ser Asp Leu Ser Ser Ala
    130                 135                 140

Tyr Ala Ile Arg Leu Tyr Glu Leu Leu Ile Cys Trp Arg Ser Thr Gly
145                 150                 155                 160

Lys Thr Pro Ile Ile Gly Leu Gly Glu Phe Arg Asn Arg Val Gly Val
                165                 170                 175

Leu Asp Ser Glu Tyr His Arg Ile Ala His Leu Lys Glu Arg Val Ile
            180                 185                 190

Glu His Ser Ile Lys Gln Ile Asn Glu His Thr Asp Ile Thr Ala Thr
        195                 200                 205

Tyr Glu Gln His Lys Lys Gly Arg Thr Ile Thr Gly Phe Ser Phe Lys
    210                 215                 220

Phe Lys Gln Lys Lys Pro Lys Gln Ala Glu Ile Ala Thr Glu Thr Pro
225                 230                 235                 240

Lys Thr Ala Thr Asn Asp Pro Asp Thr Thr Lys Pro Leu Thr Glu Pro
                245                 250                 255

Gln Ile Ala Lys Tyr Ser Met Ile Leu Cys Lys Leu Gly Ser Ile Ser
            260                 265                 270

Asp Leu Ser Asn Phe Pro Asp Tyr Pro Ala Phe Ala Asn Trp Ile Gly
        275                 280                 285

Asn Ile Leu Arg Asn Pro Glu Lys Ala Asp Glu Gln Ile Ala Lys Arg
    290                 295                 300

Ile Phe Thr Ala Leu Lys Thr Glu Thr Asp Tyr Ser Lys Lys Asn
305                 310                 315

<210> SEQ ID NO 9
<211> LENGTH: 7
<212> TYPE: PRT
<213> ORGANISM: artificial sequence
<220> FEATURE:
<223> OTHER INFORMATION: MSBI1 epitope

<400> SEQUENCE: 9

Asn Arg Leu Ser Asp Arg Phe
1               5

<210> SEQ ID NO 10
<211> LENGTH: 326
<212> TYPE: PRT
<213> ORGANISM: artificial
<220> FEATURE:
<223> OTHER INFORMATION: CMI1.252

<400> SEQUENCE: 10

Met Ser Asp Leu Ile Val Lys Asp Asn Ala Leu Met Asn Ala Ser Tyr
1               5                   10                  15

Asn Leu Ala Leu Val Glu Gln Arg Leu Ile Leu Leu Ala Ile Leu Glu
            20                  25                  30

Ala Arg Glu Thr Gly Lys Gly Ile Asn Ala Asn Asp Pro Leu Thr Val
        35                  40                  45

His Ala Ser Ser Tyr Ile Asn Gln Phe Asn Val Glu Arg His Thr Ala
    50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ile Asn Ile Thr Ser Arg
                85                  90                  95

Trp Val Ser Gln Ile Gly Tyr Met Asp Asp Thr Ala Thr Val Glu Ile
            100                 105                 110

Ile Phe Ala Pro Ala Val Val Pro Leu Ile Thr Arg Leu Glu Glu Gln
        115                 120                 125

Phe Thr Gln Tyr Asp Ile Glu Gln Ile Ser Glu Leu Ser Ser Ala Tyr
    130                 135                 140

Ala Val Arg Leu Tyr Glu Leu Leu Ile Cys Trp Arg Ser Thr Gly Lys
145                 150                 155                 160

Thr Pro Ile Ile Asp Leu Thr Glu Phe Arg Lys Arg Leu Gly Val Leu
                165                 170                 175

Asp Thr Glu Tyr Thr Arg Thr Asp Asn Leu Lys Met Arg Val Ile Glu
            180                 185                 190

Leu Gly Leu Lys Gln Ile Asn Glu His Thr Asp Ile Thr Ala Ser Tyr
        195                 200                 205

Glu Gln His Lys Lys Gly Arg Thr Ile Thr Gly Phe Ser Phe Lys Phe
    210                 215                 220

Lys Gln Lys Lys Lys Thr Gly Ala Glu Met Pro Lys Asn Ser Asp Ser
225                 230                 235                 240

Ser Pro His Ile Glu Lys Pro Ser Gln Ile Pro Ala Asn Ile Ala Lys
                245                 250                 255

Gln Pro Glu Asn Ala Lys Lys Asp Asp Leu Gly His Arg Ala Ser Lys
            260                 265                 270

Ile Thr Gly Leu Ile Met Ser Asn Gly Leu Ala Asp Arg Phe Lys Arg
        275                 280                 285

Gly Asp Glu Ser Val Ile Asp Met Met Lys Arg Ile Lys Glu Glu Ile
    290                 295                 300

Thr Thr Asp Thr Thr Ala Asp Gln Trp Glu Asn Lys Leu Glu Glu Phe
305                 310                 315                 320

Gly Val Ile Phe Gln Ser
                325

<210> SEQ ID NO 11
<211> LENGTH: 324
<212> TYPE: PRT
<213> ORGANISM: artificial
<220> FEATURE:
<223> OTHER INFORMATION: CMI2.214

<400> SEQUENCE: 11

```
Met Ser Asp Leu Ile Val Lys Asp Asn Ala Leu Met Asn Ala Ser Tyr
1               5                   10                  15

Asn Leu Asp Leu Val Glu Gln Arg Leu Ile Leu Ala Ile Leu Glu
            20                  25                  30

Ala Arg Glu Thr Gly Lys Gly Ile Asn Ala Asn Asp Pro Leu Thr Val
            35                  40                  45

His Ala Glu Ser Tyr Ile Asn Gln Phe Gly Val Ala Arg Gln Thr Ala
        50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ala Asn Ile Thr Ser Arg
                85                  90                  95

Trp Val Ser Gln Ile Ala Tyr Ile Asp Glu Thr Ala Thr Val Glu Val
            100                 105                 110

Ile Phe Ala Pro Ala Val Val Pro Leu Ile Thr Arg Leu Glu Glu Gln
        115                 120                 125

Phe Thr Gln Tyr Asp Ile Glu Gln Ile Ser Gly Leu Ser Ser Ala Tyr
130                 135                 140

Ala Val Arg Leu Tyr Glu Leu Leu Ile Cys Trp Arg Ser Thr Gly Lys
145                 150                 155                 160

Thr Pro Val Ile Glu Leu Ala Glu Phe Arg Lys Arg Leu Gly Val Leu
                165                 170                 175

Asn Asp Glu Tyr Thr Arg Ser Asp Asn Phe Lys Lys Trp Ile Ile Glu
            180                 185                 190

Asn Pro Ile Lys Gln Ile Asn Glu His Thr Asp Ile Thr Ala Ser Tyr
        195                 200                 205

Glu Gln His Lys Lys Gly Arg Thr Ile Thr Gly Phe Ser Phe Lys Phe
210                 215                 220

Lys Gln Lys Lys Lys Thr Glu Pro Glu Thr Pro Lys Asn Ser Asp Ser
225                 230                 235                 240

Ser Gln Arg Ile Glu Lys Pro Ser Gln Ile Pro Ala Asn Ile Val Lys
                245                 250                 255

Gln Pro Glu Asn Ala Asn Leu Ser Asp Leu Gln His Arg Ala Ser Lys
            260                 265                 270

Ile Thr Gly Leu Ile Met Ser Asn Arg Leu Ser Asp Arg Phe Lys Gln
        275                 280                 285

Gly Asp Glu Ser Ile Met Gln Met Met Ala Arg Ile Gln Ser Glu Ile
290                 295                 300

Thr Thr Asp Ser Ile Ala Asp Gln Trp Gln Ser Lys Leu Glu Glu Phe
305                 310                 315                 320

Gly Val Val Phe
```

<210> SEQ ID NO 12
<211> LENGTH: 324
<212> TYPE: PRT
<213> ORGANISM: artificial
<220> FEATURE:
<223> OTHER INFORMATION: CMI3.168

<400> SEQUENCE: 12

```
Met Ser Asp Leu Ile Val Lys Asp Asn Ala Leu Met Asn Ala Ser Tyr
1               5                   10                  15

Asn Leu Ala Leu Val Glu Gln Arg Leu Ile Leu Leu Ala Ile Leu Glu
            20                  25                  30

Ala Arg Glu Thr Gly Lys Gly Ile Asn Ala Asn Asp Pro Leu Thr Val
        35                  40                  45

His Ala Ser Ser Tyr Ile Asn Gln Phe Asn Val Glu Arg His Thr Ala
    50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ala Asn Ile Thr Ser Arg
                85                  90                  95

Trp Val Ser Gln Ile Ala Tyr Ile Asp Glu Thr Ala Thr Val Glu Val
            100                 105                 110

Ile Phe Ala Pro Ala Val Val Pro Leu Ile Thr Arg Leu Glu Glu Gln
        115                 120                 125

Phe Thr Gln Tyr Asp Ile Glu Gln Ile Ser Gly Leu Ser Ser Ala Tyr
130                 135                 140

Ala Val Arg Leu Tyr Glu Leu Leu Ile Cys Trp Arg Thr Thr Gly Lys
145                 150                 155                 160

Thr Pro Val Leu Asp Leu Thr Glu Phe Arg Lys Arg Leu Gly Val Leu
                165                 170                 175

Asp Thr Glu Tyr Thr Arg Thr Asp Asn Leu Lys Met Arg Val Ile Glu
            180                 185                 190

Gln Ser Leu Lys Gln Ile Asn Lys His Thr Asp Ile Thr Ala Ser Tyr
        195                 200                 205

Glu Gln His Lys Lys Gly Arg Thr Ile Thr Gly Phe Ser Phe Lys Phe
210                 215                 220

Lys Gln Lys Lys Lys Thr Glu Pro Glu Thr Pro Lys Asn Asn Asp Ser
225                 230                 235                 240

Gly Val Ser Lys Pro Lys Thr Val Glu Ile Pro Ala Glu Val Val Lys
                245                 250                 255

Gln Pro Lys Asn Thr Asn Leu Ser Asp Leu Glu Lys Arg Val Arg Met
            260                 265                 270

Ile Thr Gly Ala Ile Ala Lys Asn Asn Leu Ala Ser Arg Phe Gln His
        275                 280                 285

Gly Asn Glu Ser Pro Leu Asp Met Met Lys Arg Ile Gln Ser Glu Ile
290                 295                 300

Thr Ser Asp Glu Thr Ala Asp Leu Trp Gln Asn Lys Leu Glu Ser Met
305                 310                 315                 320

Gly Val Val Phe
```

<210> SEQ ID NO 13
<211> LENGTH: 999
<212> TYPE: DNA
<213> ORGANISM: artificial sequence
<220> FEATURE:
<223> OTHER INFORMATION: codon-optimized MSBI1

<400> SEQUENCE: 13

```
atgagcgacc tgatcgtgaa agacaatgcc ctgatgaacg cctcctacaa cctggcactg    60
gtcgaacaga gactgattct gctggctatc atcgaggcaa gggagaccgg caagggcatc   120
```

```
aacgccaatg accccctgac agtgcacgcc agctcctaca tcaaccagtt taatgtggag    180
cgccacaccg cctatcaggc cctgaaggac gcctgcaagg atctgtttgc ccggcagttc    240
agctaccagg agaagcggga gagaggcagg atcaacatca aagcagatg ggtgtcccag    300 atcggctata tggacgatac cgccacagtg gagatcatct ttgcaccagc agtggtgcct    360
ctgatcacca ggctggagga gcagttcaca cagtacgaca tcgagcagat ctccggactg    420
tctagcgcct acgccgtgcg catgtatgag ctgctgatct gttggcggtc taccggcaag    480
acacctatca tcgagctgga tgagttccgc aagcggatcg gcgtgctgga caccgagtac    540
accagaacag ataacctgaa gatgagagtg atcgagctgg ccctgaagca gatcaatgag    600
cacaccgata tcacagcctc ttatgagcag acaagaagg gccgcgtgat caccggcttc    660
agctttaagt tcaagcacaa gaagcagaac tctgacaaga caccaaagaa tagcgattcc    720
tctccccgga tcgtgaagca cagccagatc cctaccaaca tcgtgaagca gccagagaat    780
gccaagatgt ccgacctgga gcacagggca tctagggtga caggcgagat catgagaaat    840
aggctgagcg atcggttcaa gcagggcgac gagtccgcca tcgatatgat gaagagaatc    900
cagtccgaga tcatcaccga cgccatcgcc gatcagtggg aatctaaact ggaagagttt    960
ggagtcgtgt ttggagcaca tcaccatcat catcactga    999
```

<210> SEQ ID NO 14
<211> LENGTH: 326
<212> TYPE: PRT
<213> ORGANISM: artificial sequence
<220> FEATURE:
<223> OTHER INFORMATION: MSBI1 protein

<400> SEQUENCE: 14

```
Met Ser Asp Leu Ile Val Lys Asp Asn Ala Leu Met Asn Ala Ser Tyr
1               5                   10                  15

Asn Leu Ala Leu Val Glu Gln Arg Leu Ile Leu Leu Ala Ile Ile Glu
            20                  25                  30

Ala Arg Glu Thr Gly Lys Gly Ile Asn Ala Asn Asp Pro Leu Thr Val
        35                  40                  45

His Ala Ser Ser Tyr Ile Asn Gln Phe Asn Val Glu Arg His Thr Ala
    50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ile Asn Ile Thr Ser Arg
                85                  90                  95

Trp Val Ser Gln Ile Gly Tyr Met Asp Asp Thr Ala Thr Val Glu Ile
            100                 105                 110

Ile Phe Ala Pro Ala Val Val Pro Leu Ile Thr Arg Leu Glu Glu Gln
        115                 120                 125

Phe Thr Gln Tyr Asp Ile Glu Gln Ile Ser Gly Leu Ser Ser Ala Tyr
    130                 135                 140

Ala Val Arg Met Tyr Glu Leu Leu Ile Cys Trp Arg Ser Thr Gly Lys
145                 150                 155                 160

Thr Pro Ile Ile Glu Leu Asp Glu Phe Arg Lys Arg Ile Gly Val Leu
                165                 170                 175

Asp Thr Glu Tyr Thr Arg Thr Asp Asn Leu Lys Met Arg Val Ile Glu
            180                 185                 190

Leu Ala Leu Lys Gln Ile Asn Glu His Thr Asp Ile Thr Ala Ser Tyr
        195                 200                 205
```

| Glu | Gln | His | Lys | Lys | Gly | Arg | Val | Ile | Thr | Gly | Phe | Ser | Phe | Lys | Phe |
| | 210 | | | | 215 | | | | 220 | | | | | | |

| Lys | His | Lys | Lys | Gln | Asn | Ser | Asp | Lys | Thr | Pro | Lys | Asn | Ser | Asp | Ser |
| 225 | | | | | 230 | | | | 235 | | | | | 240 | |

| Ser | Pro | Arg | Ile | Val | Lys | His | Ser | Gln | Ile | Pro | Thr | Asn | Ile | Val | Lys |
| | | | | 245 | | | | | 250 | | | | | 255 | |

| Gln | Pro | Glu | Asn | Ala | Lys | Met | Ser | Asp | Leu | Glu | His | Arg | Ala | Ser | Arg |
| | | | 260 | | | | | 265 | | | | | 270 | | |

| Val | Thr | Gly | Glu | Ile | Met | Arg | Asn | Arg | Leu | Ser | Asp | Arg | Phe | Lys | Gln |
| | | 275 | | | | | 280 | | | | | 285 | | | |

| Gly | Asp | Glu | Ser | Ala | Ile | Asp | Met | Met | Lys | Arg | Ile | Gln | Ser | Glu | Ile |
| | 290 | | | | 295 | | | | 300 | | | | | | |

| Ile | Thr | Asp | Ala | Ile | Ala | Asp | Gln | Trp | Glu | Ser | Lys | Leu | Glu | Glu | Phe |
| 305 | | | | 310 | | | | | 315 | | | | | 320 | |

| Gly | Val | Val | Phe | Gly | Ala |
| | | | | 325 | |

<210> SEQ ID NO 15
<211> LENGTH: 974
<212> TYPE: DNA
<213> ORGANISM: artificial sequence
<220> FEATURE:
<223> OTHER INFORMATION: MSBI1 wild type

<400> SEQUENCE: 15

| atgagcgatt | taatagtaaa | agataacgcc | ctaatgaatg | ctagttataa | cttagctttg | 60 |
| gttgaacaga | ggttaattct | attagcaatc | atagaagcga | gagaaacagg | caaagggatt | 120 |
| aatgccaatg | atcctttaac | agttcatgca | agtagctata | tcaatcaatt | taacgtagaa | 180 |
| aggcatacgg | catatcaagc | cctcaaagat | gcttgtaaag | acttgtttgc | ccgtcaattc | 240 |
| agttaccaag | aaaagcgaga | acgaggacga | attaatatta | caagtcgatg | ggtttcgcaa | 300 |
| attggctata | tggacgatac | agcaaccgtt | gagattattt | ttgcccctgc | ggttgttcct | 360 |
| ctgattacac | ggctagagga | acagttcacc | cagtacgata | ttgagcaaat | tagcggttta | 420 |
| tcgagtgcat | atgctgttcg | tatgtacgaa | ctgctgattt | gttggcgtag | cacaggcaaa | 480 |
| acaccaatta | ttgagctaga | cgagtttaga | aagcgaatag | gtgttttaga | tactgaatac | 540 |
| actagaacag | ataatttaaa | gatgcgagtt | attgaattag | ccctaaaaca | aatcaacgaa | 600 |
| catacagaca | tcacagcaag | ctatgaacaa | cacaaaaaag | ggcgagtgat | tacaggattc | 660 |
| tcattcaagt | ttaagcacaa | gaaacaaaac | agcgataaaa | cgccaaaaaa | tagcgattct | 720 |
| agcccacgta | tcgtaaaaca | tagtcaaatc | cctccaacat | tgtaaaacag | cctgaaaacg | 780 |
| ccaaaatgag | cgatttagaa | catagagcga | gccgtgttac | aggggaaata | atgcgaaatc | 840 |
| gtctgtcaga | tcggtttaaa | caaggcgatg | aatcagcaat | cgacatgatg | aaacgtattc | 900 |
| aaagtgaaat | aataaccgat | gcaatagcag | accagtggga | aagcaaactg | gaggagtttg | 960 |
| gcgtggtttt | ttag | | | | | 974 |